United States Patent [19]

Yokose et al.

[11] Patent Number: 4,864,023

[45] Date of Patent: Sep. 5, 1989

[54] PYRIDO(3,2,1-IJ)-1,3,4-BENZOXADIAZINE DERIVATIVES

[75] Inventors: Kazuteru Yokose, Urayasu; Nobuo Shimma; Mikayo Kamata, both of Chigasaki; Masahiro Aoki; Tatsuo Ohtsuka, both of Fujisawa, all of Japan

[73] Assignee: Hoffmann-La Roche Inc., Nutley, N.J.

[21] Appl. No.: 236,822

[22] Filed: Aug. 26, 1988

Related U.S. Application Data

[62] Division of Ser. No. 94,361, Sep. 8, 1987, Pat. No. 4,801,584.

[51] Int. Cl.$^4$ ............................................. C07D 498/06
[52] U.S. Cl. ......................................................... 544/66
[58] Field of Search ............................................ 544/66

[56] References Cited

U.S. PATENT DOCUMENTS 4,382,892 5/1983 Hayakawa et al. ............ 544/101 X
4,666,920 5/1987 Grohe et al. ...................... 514/312

FOREIGN PATENT DOCUMENTS 198685 9/1987 Japan .

OTHER PUBLICATIONS

Masuzawa et al., Chemical Abstracts, vol. 108 (1988) 112,468p.

Primary Examiner—Richard L. Raymond
Attorney, Agent, or Firm—Jon S. Saxe; Bernard S. Leon; A. Kate Huffman

[57] ABSTRACT

The invention is concerned with tricyclic compounds of the formula

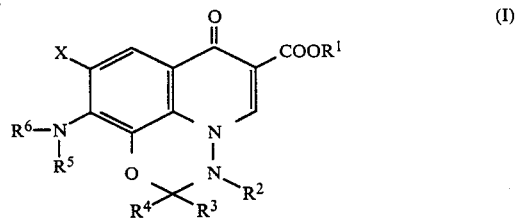

wherein $R^1$ is a hydrogen atom or a carboxy-protecting radical; $R^2$ is a hydrogen atom or a lower alkyl radical which may be substituted with a halogen atom; $R^3$ and $R^4$ independently are a hydrogen atom or a lower alkyl radical which may be substituted with a hydroxy radical or a substituted or unsubstituted amino radical; X is a halogen atom; and $R^5$ and $R^6$ are independently a hydrogen atom or a lower alkyl radical which may be substituted with a hydroxy radical, a lower alkoxy radical or a substituted or unsubstituted amino radical; or $R^5$ and $R^6$, taken together with the adjacent nitrogen atom, may form a 5 to 7 membered heterocyclic ring which may be substituted with one or more substituents at the carbon atom(s), and the heterocyclic ring may further contain $-NR^7-$, $-O-$, $-S-$, $-SO-$, $-SO_2-$ or $-NR^7-CO-$, and also $R^7$ is a hydrogen atom, a lower alkenyl radical, a lower alkyl or aralkyl radical which may be substituted, or a radical represented by the formula

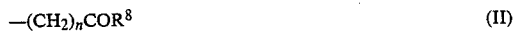

in which n is an integer from 0 to 4 and $R^8$ is a hydrogen atom, a lower alkoxy radical, or an amino, lower alkyl or aryl radical which may be substituted, as well as pharmaceutically acceptable salts thereof, and hydrates or solvates of the compounds of the formula I or their salts.

Also included is a process for the manufacture of these compounds, pharmaceutical preparations containing them, intermediates useful in said process, and methods of using them. The end products have antimicrobial activity.

1 Claim, No Drawings

PYRIDO(3,2,1-IJ)-1,3,4-BENZOXADIAZINE DERIVATIVES

This is a division of application Ser. No. 094,361, filed 9/8/87, now U.S. Pat. No. 4,801,584.

FIELD OF THE INVENTION

The present invention relates to novel tricyclic compounds, more particularly to pyrido[3,2,1-ij]-1,3,4-benzoxadiazine derivatives, to a process for their manufacture, to pharmaceutical preparations containing them, to intermediates useful in said process, and to methods of using them.

SUMMARY OF THE INVENTION

The present invention relates to novel pyrido[3,2,1-ij]-1,3,4-benzoxadiazine derivatives represented by the formula

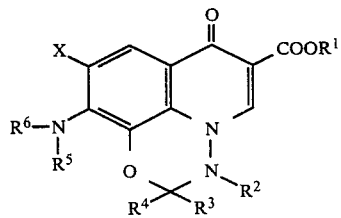

wherein $R^1$ is a hydrogen atom or a carboxy-protecting radical; $R^2$ is a hydrogen atom or a lower alkyl radical which may be substituted with a halogen atom; $R^3$ and $R^4$ independently are a hydrogen atom or a lower alkyl radical which may be substituted with a hydroxy radical or a substituted or unsubstituted amino radical; X is a halogen atom; and $R^5$ and $R^6$ are independently a hydrogen atom or a lower alkyl radical which may be substituted with a hydroxy radical, a lower alkoxy radical or a substituted or unsubstituted amino radical; or $R^5$ and $R^6$, taken together with the adjacent nitrogen atom, may form a 5 to 7 membered heterocyclic ring which may be substituted with one or more substituents at the carbon atom(s), and the heterocyclic ring may further contain $-NR^7-$, $-O-$, $-S-$, $-SO-$, $-SO_2-$ or $-NR^7-CO-$, and also $R^7$ is a hydrogen atom, a lower akenyl radical, a lower alkyl or aralkyl radical which may be substituted, or a radical represented by the formula $$-(CH_2)_nCOR^8 \qquad (II)$$

in which n is an integer from 0 to 4 and $R^8$ is a hydrogen atom, a lower alkoxy radical, or an amino, lower alkyl or aryl radical which may be substituted, as well as pharmaceutically acceptable salts thereof, and hydrates or solvates of the compounds of the formula I or their salts, which are useful as effective ingredients in antibacterial agents.

DETAILED DESCRIPTION

The respective radicals of the formula I which are defined above are explained in more detail as follows; reference to the term "lower" is intended to mean a carbon chain preferably containing up to and including 7 carbon atoms, unless otherwise indicated.

Explanation of $R^1$:

$R^1$ is a hydrogen atom or a carboxy-protecting radical.

In the above, the carboxy-protecting radical means any conventional moiety for protecting a carboxy group during reaction which are known to chemists skilled in the antibacterial art e.g. lower alkyl such as methyl, ethyl, n-propyl, t-butyl; other meanings are e.g. in vivo readily hydrolyzable carboxy-protecting radicals such as lower alkanoyloxyalkyl (e.g. acetoxymethyl, pivaloyloxymethyl, 1-acetoxyethyl and 1-pivaloyloxyethyl); lower alkoxycarbonyloxyalkyl (e.g. methoxycarbonyloxymethyl, 1-ethoxycarbonyloxyethyl and 1-isopropoxycarbonyloxyethyl); lactonyl (e.g. phthalidyl and thiophthalidyl); lower alkoxymethyl (e.g. methoxymethyl); benzyloxymethyl; (5-methyl-2-oxo-1,3-dioxol-4-yl)methyl; or lower alkanoylaminomethyl (e.g. acetamidomethyl). Other ester groups e.g. benzyl, cyanomethyl, phenacyl, phenyl and the like can also be used.

Explanation of $R^2$:

$R^2$ is a hydrogen atom or a lower alkyl radical which may be substituted with a halogen atom.

In the above, the lower alkyl radical preferably contains 1 to 4 carbon atoms, especially methyl, ethyl, n-propyl, iso-propyl, n-butyl and the like, and the halogen atom is fluorine, chlorine or bromine, preferably fluorine.

Explanation of $R^3$ and $R^4$:

$R^3$ and $R^4$ independently are a hydrogen atom or a lower alkyl radical which may be substituted with a hydroxy radical or a substituted or unsubstituted amino radical.

In the above, the lower alkyl radicals preferably contain 1 to 4 carbon atoms, especially methyl, ethyl, n-propyl, iso-propyl, n-butyl, and the like. The substituted amino radicals can be di-lower alkylamino such as dimethylamino, diethylamino; lower alkylamino such as methylamino, ethylamino, lower cycloalkylamino such as cyclopropylamino and the like.

Explanation of $R^5$ and $R^6$:

$R^5$ and $R^6$ independently are a hydrogen atom or a lower alkyl radical which may be substituted with a hydroxy radical, a lower alkoxy radical or a substituted or unsubstituted amino radical; or $R^5$ and $R^6$, taken together with the adjacent nitrogen atom, may form a 5 to 7 membered heterocyclic ring which may be substituted with one or more substituents at the carbon atom(s), and the heterocyclic ring may further contain $-NR^7-$, $-O-$, $-S-$, $-SO-$, $-SO_2-$ or $-NR^7-CO-$ and also $R^7$ is a hydrogen atom, a lower alkenyl radical, a lower alkyl or aralkyl radical which may be substituted, or a radical represented by the formula $$-(CH_2)_nCOR^8 \qquad (II)$$

in which n is an integer from 0 to 4 and $R^8$ is a hydrogen atom, a lower alkoxy radical, or an amino, lower alkyl or aryl radical which may be substituted.

The above defined radicals will be further illustrated in more detail as follows:

The lower alkyl radical preferably contains 1 to 4 carbon atoms, such as methyl, ethyl, n-propyl, iso-propyl, n-butyl, and the like. The lower alkoxy radical preferably contains 1 to 4 carbon atoms such as methoxy, ethoxy, n-propoxy, iso-propoxy, n-butoxy, and the like. The substituted amino radical can be di-lower alkylamino such as dimethylamino, diethylamino, ethylmethylamino; lower alkylamino such as methylamino, ethylamino, n-propylamino, iso-propylamino; lower cycloalkylamino such as cyclopropylamino and the like.

The 5 to 7 membered heterocyclic ring formed by $R^5$ and $R^6$ can be piperazinyl, morpholinyl, thiomorpholinyl, piperidyl, homopiperazinyl, pyrrolidinyl, pyrrolinyl, pyrrolyl, imidazolyl, triazolyl and the like. Examples of the substituents at the carbon atom(s) of the heterocyclic ring are hydroxy, lower alkoxy such as methoxy, ethoxy, n-propoxy; amino; lower alkylamino such as methylamino, ethylamino, n-propylamino, iso-propylamino; lower cycloalkylamino such as cyclopropylamino; di-lower alkylamino such as dimethylamino, diethylamino, ethylmethylamino; lower alkanoylamino such as acetylamino; benzylamino optionally substituted by nitro, amino, halogen, hydroxy and/or lower alkoxy, e.g. (4-aminobenzyl)amino; a group of the formula

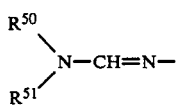

where $R^{50}$ and $R^{51}$ are lower alkyl or together with the nitrogen atom represent a 5 to 8 membered saturated N-heterocycle such as (dimethylamino)methyleneamino, (hexahydro-1H-azepin-1-yl)methyleneamino; benzyloxycarbonylamino; halogen, such as fluoro, chloro, bromo; lower alkyl such as methyl, ethyl, n-propyl, iso-propyl; amino-lower alkyl, lower alkylamino-lower alkyl, lower cycloalkylamino-lower alkyl, di-lower alkylamino-lower alkyl, lower alkanoylamino-lower alkyl, examples of these substituents being: aminomethyl, (methylamino)methyl, (ethylamino)methyl, (n-propylamino)methyl, (iso-propylamino)methyl, (cyclopropylamino)methyl, (dimethylamino)methyl, (diethylamino)methyl, (ethylmethylamino)methyl, acetylaminomethyl, 2-aminoethyl, 2-(methylamino)ethyl, 2-(ethylamino)ethyl, 2-(diethylamino)ethyl, 2-(dimethylamino)ethyl, 2-(ethylmethylamino)ethyl; hydroxy-(lower alkyl) such as hydroxymethyl, 2-hydroxyethyl; phenyl, optionally substituted by amino, halogen, hydroxy and/or lower alkoxy such as 4-aminophenyl, 4-fluorophenyl, 4-chlorophenyl, 4-hydroxyphenyl, 4-methoxyphenyl; a heterocyclic ring such as pyrrolyl, 4-methyl-1-piperazinyl and the like.

The lower alkenyl radical represented by $R^7$ is e.g. allyl, 3-methyl-2-butenyl, 2-butenyl, 1-methyl-2-propenyl, 3-butenyl and the like.

The substituted alkyl radical represented by $R^7$ is e.g. hydroxy-(lower alkyl) such as 2-hydroxyethyl, 3-hydroxybutyl; lower alkoxy-lower alkyl such as 2-methoxyethyl, 2-ethoxyethyl; amino-lower alkyl such as 2-aminoethyl, 3-aminobutyl; lower alkylamino-lower alkyl such as 2-(methylamino)ethyl, 2-(ethylamino)ethyl, 3-(methylamino)butyl, 3-(ethylamino)butyl; di-lower alkylamino-lower alkyl such as 2-(dimethylamino)ethyl, 2-(diethylamino)ethyl, 3-(dimethylamino)butyl, 3-(diethylamino)butyl; halogen-lower alkyl such as 2-fluoroethyl, 3-fluoro-n-butyl; carboxy-lower alkyl such as carboxymethyl, 2-carboxyethyl; sulfo-lower alkyl such as sulfomethyl, 2-sulfoethyl and the like.

The aralkyl radical $R^7$ which may be substituted is e.g. benzyl and $R^7$ can be substituted by one or more amino, nitro, lower alkylamino, di-lower alkylamino, halogen and/or lower alkoxy group(s) such as 4-aminobenzyl, 4-nitrobenzyl, 4-(dimethylamino)benzyl, 4-fluorobenzyl, 4-chlorobenzyl, 3-methoxybenzyl, 4-methoxybenzyl, 3,4-dimethoxybenzyl and the like.

The amino radical $R^8$ may be unsubstituted or substituted by e.g. lower alkyl such as methylamino, dimethylamino, or by lower cycloalkyl such as cyclopropylamino.

A lower alkyl radical $R^8$ may likewise be unsubstituted or substituted. The substituted alkyl radical represented by $R^8$ is e.g. carrying a carboxy or lower alkoxycarbonyl radical such as in 2-carboxyethyl, 3-carboxy-n-propyl, 2-methoxycarbonylethyl, 2-ethoxycarbonylethyl, 3-methoxycarbonyl-n-propyl and the like.

The aryl radical represented by $R^8$ is preferably phenyl; substituted aryl is preferably carrying one or more halogen, lower alkoxy, hydroxy, nitro and/or amino group(s) such as in 4-fluorophenyl, 4-chlorophenyl, 4-bromophenyl, 4-methoxyphenyl, 2-carboxyphenyl, 4-hydroxyphenyl, 4-nitrophenyl, 4-aminophenyl and the like.

Especially preferable radicals represented by $R^7$ are hydrogen, methyl, ethyl, n-propyl, iso-propyl, 2-hydroxyethyl, 2-methoxyethyl, 2-aminoethyl, 3-amino-n-butyl, 2-(methylamino)ethyl, 2-(ethylamino)ethyl, 2-fluoroethyl, carboxymethyl, sulfomethyl, allyl, 4-aminobenzyl, 4-fluorobenzyl, formyl, acetyl, propionyl, benzoyl, 4-aminobenzoyl, 2-oxo-n-propyl, 2-oxo-n-butyl, 3-oxo-n-butyl, 3-oxo-n-pentyl, 3-carboxypropionyl, 3-ethoxycarbonylpropionyl, 4-carboxy-n-butyryl, phenacyl, 4'-aminophenacyl, ethoxycarbonyl, methoxycarbonyl, carbamoyl and the like.

Especially preferable radicals represented by $R^5R^6N-$ in the formula (I) are 1-piperazinyl, 4-methyl-1-piperazinyl, 3-methyl-1-piperazinyl, 3-phenyl-1-piperazinyl, 3,4-dimethyl-1-piperazinyl, 4-ethyl-1-piperazinyl, 3-(4-aminophenyl)-1-piperazinyl, 4-n-propyl-1-piperazinyl, 4-(2-fluoroethyl)-1-piperazinyl, 4-allyl-1-piperazinyl, 4-(2-oxo-n-propyl)-1-piperazinyl, 4-(carboxymethyl)-1-piperazinyl, 4-(3-oxo-n-butyl)-1-piperazinyl, 4-(sulfomethyl)-1-piperazinyl, 4-(4-aminobenzyl)-1-piperazinyl, 4-(2-hydroxyethyl)-1-piperazinyl, 3-oxo-1-piperazinyl, 4-phenacyl-1-piperazinyl, 4-(3-carboxypropionyl)-1-piperazinyl, 4-acetyl-1-piperazinyl, 4-(4-nitrobenzyl)-1-piperazinyl, morpholino, 2-methyl-4-morpholinyl, 2,6-dimethyl-4-morpholinyl, 4-thiomorpholinyl, 1-oxide-4-thiomorpholinyl, 1,1-dioxide-4-thiomorpholinyl, 4-(aminomethyl)-1-piperidyl, 4-[(methylamino)methyl]-1-piperidyl, 4-methoxy-1-piperidyl, 4-hydroxy-1-piperidyl, 4-(1-pyrrolyl)-1-piperidyl, 4-amino-1-piperidyl, 4-(methylamino)-1-piperidyl, 4-(ethylamino)-1-piperidyl, 1-homopiperazinyl, 4-methyl-1-homopiperazinyl, 3-amino-1-pyrrolidinyl, 3-(methylamino)-1-pyrrolidinyl, 3-(ethylamino)-1-pyrrolidinyl, 3-(benzyloxycarbonylamino)-1-pyrrolidinyl, 3-(aminomethyl)-1-pyrrolidinyl, 3-amino-4-phenyl-1-pyrrolidinyl, 3-amino-3-methyl-1-pyrrolidinyl, 3-amino-4-methyl-1-pyrrolidinyl, 3-(4-aminobenzylamino)-1-pyrrolidinyl, 3-(4-methyl-1-piperazinyl)-1-pyrrolidinyl, 3-[(dimethylamino)methyleneamino]-1-pyrrolidinyl, 3-[(methylamino)methyl]-1-pyrrolidinyl, 3-[(methylamino)methyl]-4-phenyl-1-pyrrolidinyl, 3-methyl-3-[(methylamino)methyl]-1-pyrrolidinyl, 3-[(ethylamino)methyl]-1-pyrrolidinyl, 3-(acetylaminomethyl)-1-pyrrolidinyl, 3-[(dimethylamino)methyl]-1-pyrrolidinyl, 3-[(ethylmethylamino)methyl]-1-pyrrolidinyl, 3-amino-4-methoxy-1-pyrrolidinyl, 3-methoxy-4-(methylamino)-1-pyrrolidinyl, 3-(ethylamino)-4-methoxy-1-pyrrolidinyl, 3-amino-4-chloro-1-pyrrolidinyl, 3-chloro-4-(methylamino)-1-pyrrolidinyl, 3-chloro-4-(ethylamino)-1-pyrrolidinyl, 3-amino-4-fluoro-1-pyrrolidinyl, 3-fluoro-4-(methylamino)-1-pyrrolidinyl, 3-(ethylamino)-4-fluoro-1-pyrrolidinyl, 3-(aminomethyl)-4-chloro-1-pyrrolidinyl, 3-chloro-4-[(methylamino)methyl]-1-pyrrolidinyl, 3-chloro-4-[(ethylamino)methyl]-1-pyrrolidinyl, 3-(aminomethyl)-4-fluoro-1-pyrrolidinyl, 3-fluoro-4-[(methylamino)methyl]-1-pyrrolidinyl, 3-[(ethylamino)methyl]-4-fluoro-1-pyrrolidinyl, 3-(aminomethyl)-4-methyl-1-pyrrolidinyl, 3-methyl-4-[(methylamino)methyl]-1-pyrrolidinyl, 3-[(ethylamino)methyl]-4-methyl-1-pyrrolidinyl, 3-hydroxy-1-pyrrolidinyl, 3-methoxy-1-pyrrolidinyl, 3-chloro-1-pyrrolidinyl, 3-fluoro-1-pyrrolidinyl, 3-hydroxy-4-methoxy-1-pyrrolidinyl, 1-imidazolyl, 4-methyl-1-imidazolyl, 3-amino-4-hydroxy-1-pyrrolidinyl, 3-(methylamino)-4-hydroxy-1-pyrrolidinyl, 3-(ethylamino)-4-hydroxy-1-pyrrolidinyl, 3-(dimethylamino)-4-hydroxy-1-pyrrolidinyl, [2-(dimethylamino)ethyl]methylamino, and the like.

Explanation of X:

X is a halogen atom such as fluorine, chlorine or bromine, preferably fluorine or chlorine.

The novel pyrido[3,2,1-ij]-1,3,4-benzoxadiazine derivatives of the formula (I) and their pharmaceutically acceptable salts and hydrates or solvates thereof and of these salts are manufactured in accordance with the present invention by a process which comprises (a) reacting a compound represented by the formula

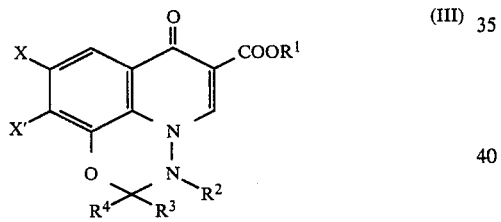

wherein $R^1$, $R^2$, $R^3$, $R^4$ and X are the same as defined above, and X' is a halogen atom; and amino, hydroxy and/or carboxy groups present may be protected, with an amine represented by the formula

wherein $R^5$ and $R^6$ are the same as defined above, followed, if necessary by removal of a protecting radical, or (b) reacting a compound represented by the formula

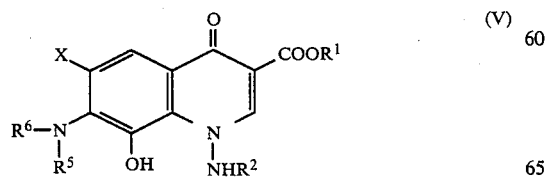

wherein $R^1$, $R^2$, $R^5$, $R^6$ and X are the same as defined above; and amino, hydroxy and/or carboxy groups present may be protected, with a carbonyl compound represented by the formula

wherein $R^3$ and $R^4$ are the same as defined above, or its polymer, acetal, ketal or enol ether, followed, if necessary, by removal of a protecting radical, or (c) for the manufacture of a compound of formula I in which $R^7$ is other than hydrogen reacting a compound of formula I in which $R^7$ is hydrogen with an agent yielding the group $R^{70}$ where $R^{70}$ is as $R^7$ but not hydrogen, or (d) for the manufacture of a compound of formula I wherein $R^5$ and/or $R^6$ are lower alkyl (or contain a di-lower alkylamino or lower alkoxy group) lower alkylating a compound of formula I wherein $R^5$ and/or $R^6$ are hydrogen or contain an amino, lower alkylamino or hydroxy group, or (e) for the manufacture of a compound of formula I in which $R^5R^6N$— is a 5 to 7 membered heterocyclic ring with —SO— or —SO$_2$— subjecting a corresponding compound wherein the heterocyclic ring contains —S— to oxidation, or (f) for the manufacture of a compound of formula I having a free amino, hydroxy and/or carboxy group splitting off the protecting group(s) from a corresponding compound of formula I having (a) protected amino, hydroxy and/or carboxy group(s), or (g) for the manufacture of a compound of formula I containing a halogen atom halogenating a correspondingly hydroxy-substituted compound of formula I in which $R^1$ is a carboxy-protecting radical and, if desired, splitting off said protecting radical $R^1$, or (h) for the manufacture of a compound of formula I containing an amino group reducing the nitro group of a correspondingly nitro-substituted compound of formula I, or (i) for the manufacture of a compound of formula I containing a group of the formula

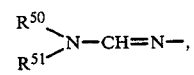

where $R^{50}$ and $R^{51}$ are lower alkyl or together with the nitrogen atom represent a 5 to 8 membered saturated N-heterocycle reacting the amino group of a correspondingly amino-substituted compound of formula I with a reactive derivative of a formamide derivative of the formula

wherein $R^{50}$ and $R^{51}$ are as above, or (j) for the manufacture of a compound of formula I in which $R^1$ is a carboxy-protecting radical subjecting a carboxylic acid of formula I to a corresponding esterification, or (k) for the manufacture of pharmaceutically acceptable salts, hydrates or solvates of a compound of formula I or hydrates or solvates of said salts converting a compound of formula I into a salt, hydrate, or solvate or into a hydrate or solvate of said salt.

Process A

As stated above, the desired compounds can be obtained by reacting a compound represented by the formula

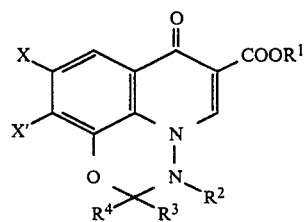

(III)

wherein $R^1$, $R^2$, $R^3$, $R^4$ and X are the same as defined above, and X' is a halogen atom, and amino, hydroxy and/or carboxy groups present may be protected, with an amine represented by the formula

(IV)

wherein $R^5$ and $R^6$ are the same as defined above, followed, if necessary, by removal of a protecting radical.

In Process A, the compound represented by the formula (III) which is used as starting compound is a novel compound, and this can be prepared, for example, according to the following reaction scheme (a) or (b).

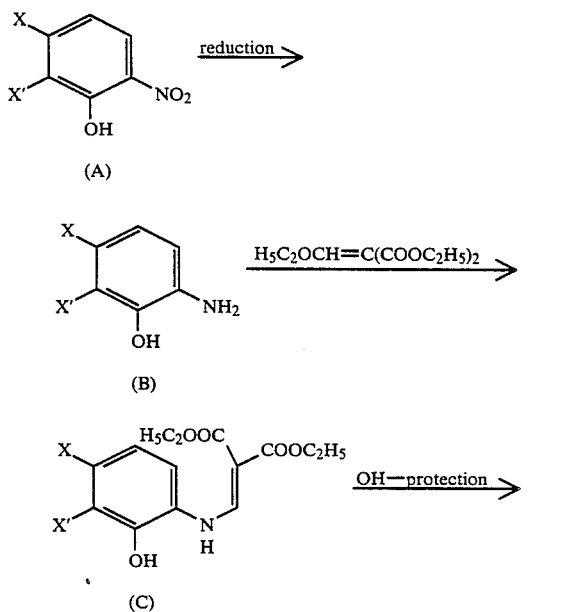

-continued
Scheme (a)

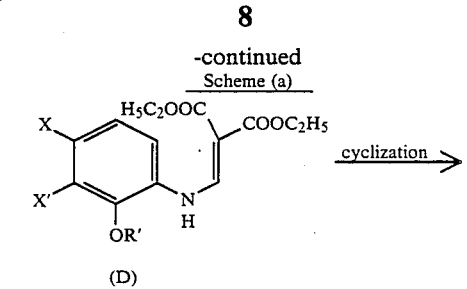

(D) cyclization →

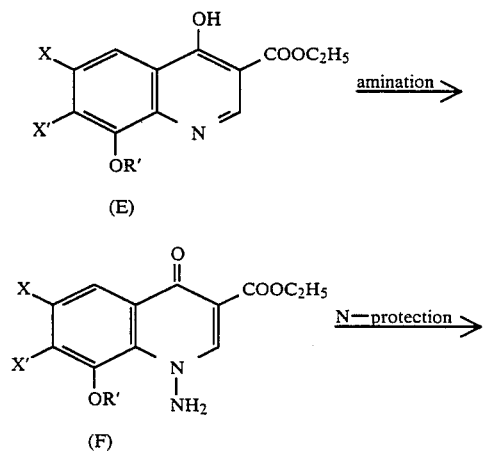

(E) amination →

(F) N—protection →

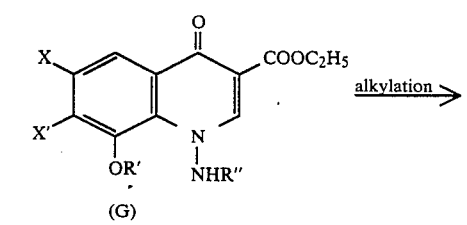

(G) alkylation →

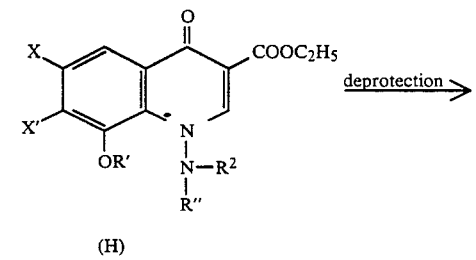

(H) deprotection →

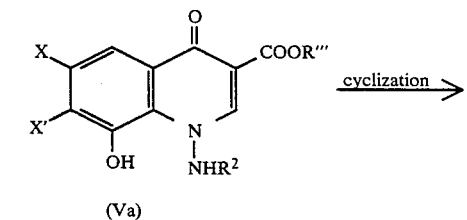

(Va) cyclization →

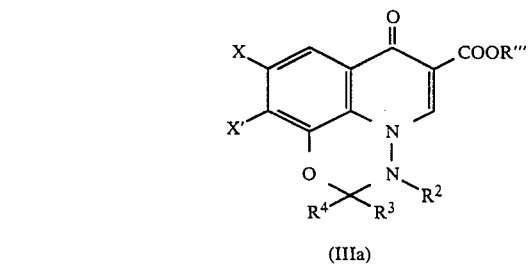

(IIIa)

Scheme (b)

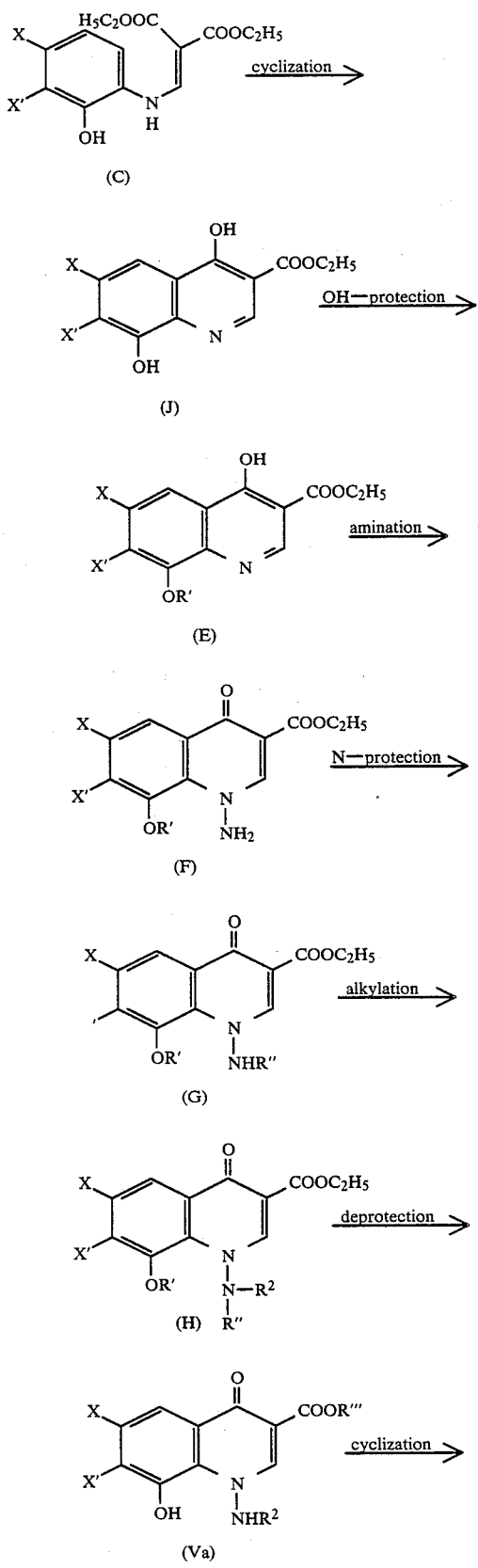

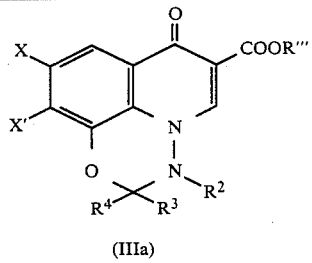

(IIIa)

wherein $R^2$, $R^3$, $R^4$, X and X' are the same as defined above; R' is a protecting radical, such as benzyl, methoxybenzyl, methoxymethyl, methoxyethoxymethyl, tetrahydropyranyl, allyl, t-butyl, t-butyldimethylsilyl, acetyl, benzoyl and the like; R" is a protecting radical, such as formyl, acetyl, trifluoroacetyl, benzoyl, ethoxycarbonyl, 2,2,2-trichloroethoxycarbonyl, phenoxycarbonyl, benzyloxycarbonyl, t-butoxycarbonyl and the like and R''' is a hydrogen atom or an ethyl radical.

If the compound of the formula (IV) contains an amino or monoalkylamino substituent, said substituent may, if desired, be protected by an amino protecting radical such as formyl, acetyl, trifluoroacetyl, benzoyl, ethoxycarbonyl, 2,2,2-trichloroethoxycarbonyl, phenoxycarbonyl, benzyloxycarbonyl, t-butoxycarbonyl and the like.

The reaction between the compound of the formula (III) and the amine of the formula (IV) or the suitably protected amine, if necessary, may be performed with or without a solvent, preferably at elevated temperature for a sufficient time so that the reaction can be substantially completed. The convenient reaction temperature is in the range of about 30° C. to about 200° C., preferably from 80° C. to 150° C. in order to obtain sufficiently fast reaction rate.

The reaction is preferably carried out in the presence of an acid acceptor such as triethylamine, pyridine, picoline, N,N-dimethylaniline, 1,8-diazabicyclo[5.4.0]undec-7-ene, 1,4-diazabicyclo[2.2.2]octane, alkali metal hydroxides, alkali metal carbonates, and the like. Alternatively an excess of the amine of the formula (IV) may be utilized as the acid acceptor.

The convenient solvents for this reaction are non-reactive solvents such as acetonitrile, alcohols, dimethylsulfoxide, dimethylformamide, dimethylacetamide, pyridine, picoline, lutidine, N,N'-dimethylpropyleneurea, and the like. Mixtures of two or more solvents may also be used.

The protecting radical may, if desired, be removed after the reaction by procedures known to those skilled in the art. For example, the formyl radical may be removed by acid or base hydrolysis preferably base hydrolysis and the benzyloxycarbonyl radical may be removed by hydrogenolysis.

The starting materials represented by the formula (III) may be exemplified as follows:
9,10-difluoro-3-methyl-7-oxo-2,3-dihydro-7H-pyrido[3,2,1-ij]-1,3,4-benzoxadiazine-6-carboxylic acid,
9,10-dichloro-3-methyl-7-oxo-2,3-dihydro-7H-pyrido[3,2,1-ij]-1,3,4-benzoxadiazine-6-carboxylic acid, 9-chloro-10-fluoro-3-methyl-7-oxo-2,3-dihydro-7H-pyrido-[3,2,1-ij]-1,3,4-benzoxadiazine-6-carboxylic acid, ethyl 9,10-difluoro-3-methyl-7-oxo-2,3-dihydro-7H-pyrido-[3,2,1-ij]-1,3,4-benzoxadiazine-6-carboxylate, benzyl 9,10-difluoro-3-methyl-7-oxo-2,3-dihydro-7H-pyrido-[3,2,1-ij]-1,3,4-benzoxadiazine-6-carboxylate, 9,10-difluoro-3-(2-fluoroethyl)-7-oxo-2,3-dihydro-7H-pyrido-[3,2,1-ij]-1,3,4-benzoxadiazine-6-carboxylic acid, 9,10-difluoro-2,3-dimethyl-7-oxo-2,3-dihydro-7H-pyrido-[3,2,1-ij]-1,3,4-benzoxadiazine-6-carboxylic acid, 9,10-difluoro-2-(hydroxymethyl)-3-methyl-7-oxo-2,3-dihydro-7H-pyrido[3,2,1-ij]-1,3,4-benzoxadiazine-6-carboxylic acid, 9,10-difluoro-2-[(dimethylamino)methyl]-3-methyl-7-oxo-2,3-dihydro-7H-pyrido[3,2,1-ij]-1,3,4-benzoxadiazine-6-carboxylic acid, 9,10-difluoro-2,2,3-trimethyl-7-oxo-2,3-dihydro-7H-pyrido-[3,2,1-ij]-1,3,4-benzoxadiazine-6-carboxylic acid, and the like.

The amine of the formula (IV) used in the above reaction is, for instance, piperazine, 4-methylpiperazine, 3-methylpiperazine, 3-phenylpiperazine, 3-(4-aminophenyl)-piperazine, 3-(4-nitrophenyl)piperazine, 4-(2-hydroxyethyl)-piperazine, morpholine, 2-methylmorpholine, 2,6-dimethylmorpholine, thiomorpholine, 4-(aminomethyl)piperidine, 4-[(methylamino)methyl]-piperidine, 4-[(ethylamino)methyl]-piperidine, 4-aminopiperidine, 4-(methylamino)piperidine, 4-(ethylamino)piperidine, 4-(benzyloxycarbonylamino)-piperidine, 4-(benzyloxycarbonylmethylamino)piperidine, 4-(benzyloxycarbonylethylamino)piperidine, 4-hydroxypiperidine, 4-methoxypiperidine, 4-(1-pyrrolyl)piperidine, homopiperazine, 3-[(methylamino)methyl]pyrrolidine, 3-[(ethylamino)methyl]pyrrolidine, 3-(acetylaminomethyl)pyrrolidine, 3-hydroxypyrrolidine, 3-methoxypyrrolidine, 3-aminopyrrolidine, 3-(benzyloxycarbonylamino)pyrrolidine, 3-(methylamino)pyrrolidine, 3-(benzyloxycarbonylmethylamino)pyrrolidine, 3-amino-4-phenylpyrrolidine, 3-amino-3-methylpyrrolidine, 3-amino-4-methylpyrrolidine, 3-(4-aminobenzylamino)-pyrrolidine, 3-(4-methyl-1-piperazinyl)pyrrolidine, 3-[(dimethylamino)methyleneamino]pyrrolidine, 3-[(methylamino)methyl]-4-phenylpyrrolidine, 3-methyl-3-[(methylamino)methyl]-pyrrolidine, 3-(ethylamino)pyrrolidine, 3-(benzyloxycarbonylethylamino)pyrrolidine, 3-[(dimethylamino)-methyl]pyrrolidine, 3-[(ethylmethylamino)methyl]-pyrrolidine, 3-azido-4-methoxypyrrolidine, 3-amino-4-methoxypyrrolidine, 3-methoxy-4-(methylamino)pyrrolidine, 3-(ethylamino)-4-methoxypyrrolidine, 3-azido-4-hydroxypyrrolidine, 3-amino-4-hydroxypyrrolidine, 3-(methylamino)-4-hydroxypyrrolidine, 3-(ethylamino)-4-hydroxypyrrolidine, 3-(aminomethyl)-4-methylpyrrolidine, 3-methyl-4-[(methylamino)methyl]pyrrolidine, 3-[(ethylamino)methyl]-4-methylpyrrolidine, 3-hydroxy-4-methoxypyrrolidine, 3-(acetylaminomethyl)-4-hydroxypyrrolidine, imidazole, 4-methylimidazole, N,N,N'-trimethylethylenediamine and the like.

Process B

The desired compound can be obtained by reacting a compound represented by the formula

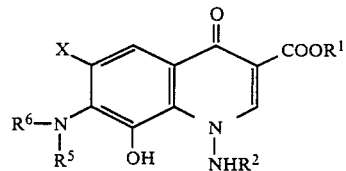

wherein $R^1$, $R^2$, $R^5$, $R^6$ and X are the same as defined above; and amino, hydroxy and/or carboxy groups present may be protected, with a carbonyl compounds represented by the formula

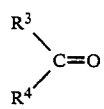

wherein $R^3$ and $R^4$ are the same as defined above, and amino groups present may be protected, or its polymer, acetal, ketal or enol ether, followed, if necessary, by removal of a protecting radical.

In Process B, the compound represented by the formula V as starting compound is a novel compound, and this compound can be produced according to the above reaction scheme (a) or (b), or reacting a compound (H) or (Va) with an amine of the formula (IV).

If the carbonyl compound of formula (VI) or its polymer, acetal, ketal or enol ether contains an amino or monoalkylamino substituent, said substituent may, if desired, be protected by a radical such as described above under R" in formulas (G) and (H).

The reaction may, if desired, be carried out in a solvent, such as dioxane, tetrahydrofuran, acetonitrile, chloroform, dimethylformamide, dimethylsulfoxide, N,N'-dimethylpropyleneurea, acetic acid and the like. Mixture of two or more solvents may also be used.

The reaction may, if necessary, be carried out in the presence of an acid catalyst such as acetic acid, hydrochloric acid, sulfuric acid, methanesulfonic acid, p-toluenesulfonic acid, pyridinium p-toluenesulfonate, ferric chloride, zinc chloride, chlorotrimethylsilane, Nafion-H (perfluorinated resin-sulfonic acid; Aldrich Chemical Co., Inc.), Amberlyst-15 (strongly acidic, macroreticular resin; Aldrich Chemical Co., Inc.), and the like.

The reaction temperature may be varied within a relatively wide range. In general, the reaction is carried out at a temperature between 20° C. and 150° C.

In a preferred embodiment of the process provided according to the present invention, about 1 mole or excess moles of the carbonyl compound of the formula (VI), or its polymer, acetal, ketal or enol ether per mole of the compound of the formula (V) is employed.

The amino or monoalkylamino protecting radical may, if desired, be removed after the reaction by the procedures known to those skilled in the art. For example, the formyl radical may be removed by acid or base hydrolysis preferably base hydrolysis and the benzyloxycarbonyl radical may be removed by hydrogenolysis.

The starting materials represented by the formula (V) may be exemplified as follows:

6,7-difluoro-8-hydroxy-1-(methylamino)-4-oxo-1,4-dihydro-3-quinolinecarboxylic acid, ethyl 6,7-difluoro-8-hydroxy-1-(methylamino)-4-oxo-1,4-dihydro-3-quinolinecarboxylate, benzyl 6,7-difluoro-8-hydroxy-1-(methylamino)-4-oxo-1,4-dihydro-3-quinolinecarboxylate,
6,7-dichloro-8-hydroxy-1-(methylamino)-4-oxo-1,4-dihydro-3-quinolinecarboxylic acid,
6-chloro-7-fluoro-8-hydroxy-1-(methylamino)-4-oxo-1,4-dihydro-3-quinolinecarboxylic acid,
6,7-difluoro-1-[(2-fluoroethyl)amino]-8-hydroxy-4-oxo-1,4-dihydro-3-quinolinecarboxylic acid,
6-fluoro-8-hydroxy-7-(1-imidazolyl)-1-(mthylamino)-4-oxo-1,4-dihydro-3-quinolinecarboxylic acid,
ethyl 6-fluoro-8-hydroxy-7-(1-imidazolyl)-1-(methylamino)-4-oxo-1,4-dihydro-3-quinolinecarboxylate,
benzyl 6-fluoro-8-hydroxy-7-(1-imidazolyl)-1-(methylamino)-4-oxo-1,4-dihydro-3-quinolinecarboxylate,
6-fluoro-1-[(2-fluoroethyl)amino]-8-hydroxy-7-(1-imidazolyl)-4-oxo-1,4-dihydro-3-quinolinecarboxylic acid,
6-chloro-8-hydroxy-7-(1-imidazolyl)-1-(methylamino)-4-oxo-1,4-dihydro-3-quinolinecarboxylic acid,
6-fluoro-8-hydroxy-1-(methylamino)-7-(4-methyl-1-piperazinyl)-4-oxo-1,4-dihydro-3-quinolinecarboxylic acid,
7-(3,4-dimethyl-1-piperazinyl)-6-fluoro-8-hydroxy-1-(methylamino)-4-oxo-1,4-dihydro-3-quinolinecarboxylic acid,
7-[3-[(benzyloxycarbonylethylamino)methyl]-1-pyrrolidinyl]-6-fluoro-8-hydroxy-1-(methylamino)-4-oxo-1,4-dihydro-3-quinoline carboxylic acid,
7-[3-(benzyloxycarbonylamino)-1-pyrrolidinyl]-6-fluoro-8-hydroxy-1-(methylamino)-4-oxo-1,4-dihydro-3-quinolinecarboxylic acid,
7-[3-[(benzyloxycarbonylmethylamino)methyl]-4-methyl-1-pyrrolidinyl]-6-fluoro-8-hydroxy-1-(methylamino)-4-oxo-1,4-dihydro-3-quinolinecarboxylic acid,
7-[3-[(benzyloxycarbonylamino)methyl]-4-chloro-1-pyrrolidinyl]-6-fluoro-8-hydroxy-1-(methylamino)-4-oxo-1,4-dihydro-3-quinolinecarboxylic acid, and the like.

Examples of compounds which can be reacted with a compound of the formula (V) are carbonyl compounds of formula (VI) such as formaldehyde, acetaldehyde, acetone, methyl ethyl ketone, and the like; their polymers such as paraformaldehyde, paracetaldehyde, trioxane, and the like; their acetals such as dimethoxymethane, 1,1-dimethoxyethane, 1,3-dioxolane, glycolaldehyde dimethylacetal, dimethylaminoacetaldehyde dimethylacetal, and the like; their ketal such as 2,2-dimethoxypropane, and the like; and their enol ether such as 2-methoxypropene, 2-trimethylsilyloxypropene and the like.

Process C

When it is desired to manufacture compounds of formula I wherein the radical $R^5R^6N-$ is a 5 to 7 membered heterocyclic ring containing a group $-NR^7-$ where $R^7$ is other than hydrogen, such as in

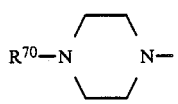  (VIII)

wherein the piperazinyl radical may be substituted at carbon atom(s), and $R^{70}$ is a lower alkenyl radical, a lower alkyl or aralkyl radical which may be substituted, or a radical represented by the formula $$-(CH_2)_nCOR^8 \qquad (II)$$

(in which n is 0 to 4 and $R^8$ is a hydrogen atom, a lower alkoxy radical or an amino, lower alkyl or aryl radical which may be substituted), the desired compound can be prepared by reacting a compound of formula I in which $R^7$ is hydrogen with an agent yielding the group $R^{70}$. This reaction, an N-alkylation (or an N-acylation), can be accomplished e.g. as follows:

N-alkylation:
A compound of the formula

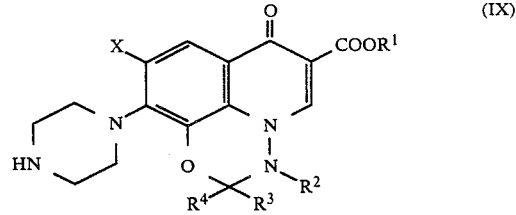  (IX)

wherein $R^1$, $R^2$, $R^3$, and $R^4$ and X are the same as defined above, the piperazinyl radical may be substituted at carbon atom(s), and amino, hydroxy and/or carboxy groups present may be protected, can be reacted
(i) with a compound represented by the formula $$R^{70}-Y \qquad (X)$$

wherein Y is a leaving group and $R^{70}$ is the same as defined above, or (for obtaining compounds where $R^7$ is the group $R^9CO-CH_2CH_2-$)
(ii) with a Michael acceptor of the formula $$R^9-CO-CH=CH_2 \qquad (XI)$$

wherein $R^9$ is a lower alkyl radical or a lower alkoxy radical, or (for obtaining compounds where $R^7$ is methyl or sulfomethyl) (iii) with formaldehyde and formic acid or an alkalimetal bisulfite.

N-Acylation:
A compound of the above formula (IX) can be reacted with an anhydride of the formula

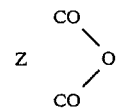  (XII)

wherein Z is an optionally substituted alkylene chain having 2 or 3 carbon atoms, or arylene radical, so as to form a compound of formula I wherein $R^7$ is $HOOC-Z-CO-$.

All these reactions are followed, if necessary, by removal of a protecting radical, if present.

Thus, the desired compound can be prepared by reacting a compound represented by the formula (IX) with a compound represented by the formula (X). As leaving group Y there may be mentioned e.g. halogen atoms such as chloro, bromo, iodo, acyloxy radicals such as acetoxy, lower alkanesulfonyloxy radicals such as methanesulfonyloxy, arylsulfonyloxy radicals such as p-toluenesulfonyloxy; optionally nitrated phenoxy radicals such phenoxy, 4-nitrophenoxy; or succinimidooxy or phthalimidooxy.

If the compound of the formula (X) contains an amino or monoalkylamino substituent, said substituent may, if desired, be protected by a radical such as described above under R'' in formulas (G) and (H).

The reaction may, if necessary, be carried out in a solvent such as dimethylformamide, dimethylacetamide, dimethylsulfoxide, N,N'-dimethylpropyleneurea, dioxane, tetrahydrofuran, pyridine and the like. Mixtures of two or more solvents may also be used.

The reaction is preferably carried out in the presence of an acid acceptor such as triethylamine, pyridine, N,N-dimethylaniline, 1,4-diazabicyclo[2.2.2]octane, 1,8-diazabicyclo[5.4.0]undec-7-ene, sodium hydride, alkali metal hydroxides, alkali metal carbonates and the like.

The reaction temperature may be varied within a relatively wide range. In general, the reaction is carried out at a temperature between about 0° C. and 180° C., preferably between 0° C. and 110° C. In carrying out the process provided according to the present invention, 1 to 4 moles, preferably 1 to 2 moles of the compound of the formula (X) is employed, based on one mole of the compound of the formula (IX).

The compound of the formula (X) used in the present invention can be iodomethane, iodoethane, bromoethane, 1-iodobutane, 1-bromobutane, 1-iodopropane, 2-iodopropane, 1-fluoro-2-iodoethane, 1-iodo-2-methoxyethane, N-(2-iodoethyl)acetamide, N-(2-iodoethyl)-N-methylacetamide, bromoacetic acid, allyl bromide, 4-fluorobenzyl bromide, acetic formic anhydride, acetic anhydride, acetyl chloride, propionic anhydride, propionyl chloride, benzoic anhydride, benzoyl chloride, 4-[(trifluoroacetyl)amino]benzoic anhydride, chloroacetone, 1-chloro-2-butanone, phenacyl chloride, 4-acetylaminophenyl chlorcmethyl ketone, ethyl chloroformate, methyl chloroformate, chloromethyl 4-nitrophenyl ketone, 4-nitrobenzyl bromide, dimethylcarbamoyl chloride and the like.

Alternatively, the desired compound can be prepared by reacting a compound of the formula (IX) with a Michael acceptor of the formula (XI).

This reaction may, if desired, be carried out in a solvent such as dimethylformamide, dimethylacetamide, dimethylsulfoxide, dioxane, tetrahydrofuran, methanol, ethanol, propanol, glycol monomethyl ether and the like. Mixtures of two or more solvents may also be used.

The reaction temperature may be varied within a relatively wide range. In general, the reaction is carried out at a temperature between about 30° C. and about 170° C., preferably between 50° C. and 140° C.

In carrying out the process provided according to the present invention preferably 1 to 5 moles, more preferably 1 to 2 moles, of the compound of the formula (XI) is employed, based on one mole of the compound of the formula (IX).

The Michael acceptor used in the present invention is e.g. methyl vinyl ketone, ethyl vinyl ketone and the like.

The reaction of compounds (IX) with formaldehyde and formic acid or an alkalimetal bisulfite (whereby compounds of formula I in which $R^7$ is methyl or sulfomethyl are obtained) is normally carried out at slightly elevated temperature, e.g. at about +50° C. to +100° C.

Moreover, the desired compound can be produced by reacting a compound of the formula (IX) with an anhydride of the formula (XII).

The reaction may, if necessary, be carried out in a solvent such as pyridine, dimethylformamide, dioxane, tetrahydrofuran and the like. Mixtures of two or more solvents may also be used.

The reaction is preferably carried out in the presence of an acid acceptor such as triethylamine, pyridine, N,N-dimethylaniline, 1,4-diazabicyclo[2.2.2]octane, alkali metal hydroxides, alkali metal carbonates and the like.

The reaction temperature may be varied within a relatively wide range. In general, the reaction is carried out at a temperature between about 0° C. and 120° C., preferably between 0° C. and 100° C.

In carrying out the process provided according to the present invention, preferably 1 mole or excess moles of the compound of the formula (XII) per mole of the compound of the formula (IX) is employed.

The anhydride used in the present invention is e.g. succinic anhydride, glutaric anhydride, N-benzyloxycarbonylaspartic anhydride, N-benzyloxycarbonylglutamic anhydride, phthalic anhydride and the like.

The protecting radical may, if desired, be removed after the reaction by the procedures known to those skilled in the art. For example, the formyl radical may be removed by acid or base hydrolysis preferably base hydrolysis and the benzyloxycarbonyl radical may be removed by hydrogenolysis.

The removal of a protecting radical may be accomplished either before or after isolating the product.

Process D

When it is desired to manufacture a compound of formula I in which $R^5$ and/or $R^6$ are lower alkyl (or contain a di-lower alkylamino or lower alkoxy group) these compounds can be manufactured by lower alkylating the corresponding non-alkylated compound viz. a compound of formula I wherein $R^5$ and/or $R^6$ are hydrogen or contain an amino, lower alkylamino or hydroxy group. The N-alkylation can be effected by reaction with a compound of the general formula

$$R^{10}Y \qquad (XIII)$$

wherein $R^{10}$ is lower alkyl and Y is a leaving group. The leaving group is of the same type as that employed in the compounds of formula (X). Also, the reaction can be carried out in the same manner as the alkylation reaction of the compounds (IX) with (X) described above. The O-alkylation is effected as the N-alkylation; however, expediently a proton acceptor such as an alkali metal hydride e.g. sodium hydride is added.

Process E

When it is desired to manufacture a compound of formula I in which $R^5R^6N-$ is a 5 to 7 membered heterocyclic ring with an $-SO-$ or $-SO_2-$ member these compounds can be manufactured by oxidizing the corresponding desoxy-compounds of formula I viz. with an $-S-$ member in the heterocycle.

The oxidation is carried out by treatment with an organic or inorganic oxidizing agent. Various compounds which readily yield oxygen can be used as the oxidizing agent; for example, organic peroxides such as monosubstituted organic peroxides (e.g. $C_1-C_4$-alkyl- or alkanoyl-hydroperoxides such as t-butylhydroperoxide), performic acid and peracetic acid, as well as phenyl-substituted derivatives of these hydroperoxides such as cumenehydroperoxide and perbenzoic acid.

The phenyl substituent can, if desired, carry a further lower group (e.g. a $C_1$–$C_4$ alkyl or alkoxy group), a halogen atom or a carboxy group (e.g. 4-methylperbenzoic acid, 4-methoxy-perbenzoic acid, 3-chloroperbenzoic acid and monoperphthalic acid). Various inorganic oxidizing agents can also be used as the oxidizing agent; for example, hydrogen peroxide, ozone, permanganates such as potassium or sodium permanganate, hypochlorites such as sodium, potassium or ammonium hypochlorite, peroxymonosulphuric and peroxydisulphuric acid. The use of 3-chloroperbenzoic acid is preferred. The oxidation is advantageously carried out in an inert solvent, for example, in an aprotic inert solvent such as tetrahydrofuran, dioxan, methylene chloride, chloroform or ethyl acetate. The oxidation is generally carried out at a temperature in the range of $-20°$ C. to $+50°$ C.

When the oxidizing agent is used in equimolar amounts or in slight excess in relation to the starting material there is mainly obtained the corresponding sulfoxide, i.e. a compound of formula I in which the heterocycle contains an —SO— member. When the amount of oxidizing agent is increased to double the stoichiometric ratio or more, there is obtained the corresponding sulfone, i.e. a compound of formula I in which the heterocycle contains an —$SO_2$— member. It is also possible to obtain the sulfone from the corresponding sulfoxide by treatment with an equimolar or greater amount of the oxidizing agent.

Proces F

When it is desired to manufacture a compound of formula I having a free amino, hydroxy and/or carboxy group these compounds can be manufactured from the corresponding compounds of formula I having one or more of any amino, hydroxy and carboxy groups present in protected form.

Amino-protecting groups are e.g. lower alkanoyl such as acetyl; benzoyl; an alkoxycarbonyl group, e.g., t-butoxycarbonyl or ethoxycarbonyl; a substituted alkoxycarbonyl group, e.g. trichloroethoxycarbonyl; phenoxycarbonyl; benzyloxycarbonyl; p-nitrobenzyloxycarbonyl; an aralkyl group such as trityl or benzhydryl; or a halogen-alkanoyl group such as trifluoroacetyl.

The amino protecting groups may be cleaved off by acid hydrolysis (e.g. the t-butoxycarbonyl or trityl group) or by basic hydrolysis (e.g. the trifluoroacetyl group). Benzyloxycarbonyl and p-nitrobenzyloxycarbonyl are removed by hydrogenolysis.

Amino-protecting groups which are cleavable by acid hydrolysis are preferably removed with the aid of a lower alkanecarboxylic acid which may be halogenated. In particular, formic acid or trifluoroacetic acid is used. The acid hydrolysis is generally carried out at room temperature, although it can be carried out at a slightly higher or slightly lower temperature (e.g. a temperature in the range of about 0° C. to +40° C.). Protecting groups which are cleavable under basic conditions are generally hydrolyzed with dilute aqueous caustic alkali at 0° C. to 30° C.

Carboxy-protecting groups are e.g. the carboxy-protecting radicals discussed under $R^1$ above.

The removal of these protecting groups can be effected in a manner known per se, e.g. by hydrogenation (benzyl) or by acidic or basic hydrolysis. The reaction is preferably effected in an inert solvent at a temperature between about 0°· C. and room temperature. Specific methods are also useful e.g: p-nitrobenzyl removed by hydrolysis in the presence of sodium sulfide at about or below 0° C. to room temperature in a solvent, such as, dimethylformamide (aqueous); t-butyl removed by reaction with trifluoroacetic acid in the presence of anisole at about 0° C. to room temperature with or without a co-solvent, such as methylene chloride; or allyl removed by a palladium (O) catalyzed transallylation reaction in the presence of sodium or potassium salt of 2-ethyl hexanoic acid, see for example J. Org. Chem. 1982, 47, 587.

Process G

When it is desired to manufacture a compound of formula I containing a halogen atom, such as a compound where $R^5R^6N$— is

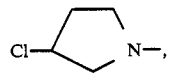

this compound can be manufactured by halogenating a correspondingly hydroxy-substituted compound (e.g. where

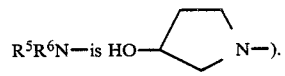

The halogenating agent is preferably a thionyl halide, especially thionyl chloride; or phosphorous trichloride, phosphorous oxychloride or phosphorous pentachloride. The reaction temperature is preferably between about 0° C. and 80° C. Carboxy groups present are preferably protected, e.g. benzylated, and subsequently, if desired, again set free e.g. by hydrogenation (removal of benzyl).

Process H

When it is desired to manufacture a compound of formula I containing an amino group such as a compound where $R^5R^6N$— is

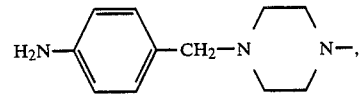

this compound can be manufactured by reducing the nitro groups of a correspondingly nitro-substituted compound of formula I. The reduction can be effected by hydrogenation in the presence of a noble metal catalyst such as palladium on charcoal. The reaction is suitably effected in water or a lower alkanol e.g. methanol or ethanol, if desired in admixture with other solvents soluble therein. The reaction temperature normally lies between about 10° C. and about 40° C., preferably at about room temperature.

Process I

When it is desired to manufacture a compound of formula I containing a group of the formula

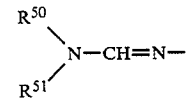

(wherein $R^{50}$ and $R^{51}$ are as above) such as a compound where $R^5R^6N-$ is

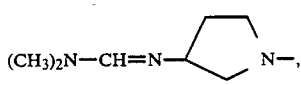

this compound can be manufactured by reacting the amino group of a correspondingly amino substituted compound of formula I (e.g. where

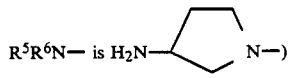

with a reactive derivative of a formamide derivative of the formula

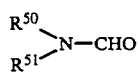

(VII)

wherein $R^{50}$ and $R^{51}$ are as above.

As reactive derivative of a compound of the formula VII can be employed the corresponding di-(lower alkyl)acetals such as the dimethyl acetals. The reaction is preferably performed in an inert solvent such as diethyl ether, dimethylformamide or dimethylsulfoxide. The temperature is preferably about room temperature but can lie well below or above, e.g. in the range of about 0° C. and 100° C.

Process J

Manufacture of esters of formula I i.e. where $R^1$ is a carboxy-protecting group can be effected by reacting a carboxylic acid of formula I with a corresponding halide, preferably an iodide or bromide, containing the desired ester group. The reactions can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0° C.–40° C.

Process K

The manufacture of the pharmaceutically acceptable salts of the compounds of formula I or the hydrates or solvates of said salts can be carried out in a manner known per se; for example, by reacting a carboxylic acid of formula I with an equivalent amount of the desired base or conversely, a free base of formula I with an organic or inorganic acid. The reaction is conveniently carried out in a solvent such as water or an organic solvent (e.g. ethanol, methanol, acetone and the like). The temperature at which the salt formation is carried out is not critical. The salt formation is generally carried out at room temperature, but it can be carried out at a temperature slightly above or below room temperature, for example in the range of 0° C. to +50° C.

Examples of therapeutically acceptable acids useful in the above process are hydrochloric, hydrobromic, sulfuric, phosphoric, nitric, formic, acetic, propionic, succinic, glycolic, lactic, malic, tartaric, citric, ascorbic, maleic, hydroxymaleic, phenylacetic, benzoic, 4-aminobenzoic, anthranilic, 4-hydroxybenzoic, salicylic, aminosalicylic, nicotinic, methanesulfonic, ethanesulfonic, hydroxyethanesulfonic, benzenesulfonic, p-toluenesulfonic, gluconic, glucuronic, galacturonic, aspartic and glutamic acid; methionine, tryptophan, lysine, arginine, and the like.

The acid addition salts can be converted into a free form by treatment with a base, such as a metal hydroxide, ammonia and the like.

The base salts of the compounds of the formula (I) can be prepared by reacting a compound of the formula (I) with a metal base or amine such as an alkali or alkaline earth metal hydroxide, or an organic amine. Examples of the metals used as cations are sodium, potassium, magnesium, calcium and the like. Examples of amines are diethanolamine, dibenzylethylenediamine, choline, ethylenediamine and the like.

The acid addition salts or base salts of the compounds of the formula (I) differ from the corresponding free form in certain physical properties such as solubility in water.

The compounds of the formula (I) and their pharmaceutically acceptable salts can exist in unsolvated as well as solvated forms, including hydrated forms. The hydration can be effected automatically in the course of the manufacturing process or can occur gradually as a result of hygroscopic properties of an initially anhydrous product. For the controlled manufacture of a hydrate a completely or partially anhydrous product can be exposed to a moist atmosphere (e.g. at about +10° C. to +40° C.). Solvates with pharmaceutically acceptable solvents such as ethanol can be obtained during e.g. crystallization.

Certain compounds provided by the present invention have asymmetric centers. The pure D isomer, pure L isomer as well as mixtures thereof, including racemic mixtures, are also contemplated by the present invention.

The compounds provided according to the present invention exhibit a broad antibacterial activity against gram-positive and gram-negative organisms and Mycoplasma and can be used as agents for treatment and prophylaxis of infectious diseases. The in vitro and in vivo antibacterial activities of the compounds of the present invention are shown as follows:

1. In Vitro Antibacterial Activities

The in vitro antibacterial activities of the representative pyrido[3,2,1-ij]-1,3,4-benzoxadiazine derivatives of the present invention were assayed by the standard agar dilution method [see: Chemotherapy, 22, 1126 (1974)]. Their minimum inhibitory concentrations (MIC, in μg/ml) are shown in Table 1 and Table 2. The compounds used here were produced by respective Examples as mentioned below.

TABLE 1

| | Antibacterial spectrum MIC (μg/ml) | | | | | | | | | | | | |
|---|---|---|---|---|---|---|---|---|---|---|---|---|---|
| | Compound (Example No.) | | | | | | | | | | | | |
| Aerobic microorganisms | 5 | 6 | 7 | 8 | 9 | 12 | 13 | 15 | 16 | 17 | 18 | 19 | 21 |

TABLE 1-continued

Antibacterial spectrum MIC (μg/ml)

| Gram-positive bacteria | | | | | | | | | | | | | |
|---|---|---|---|---|---|---|---|---|---|---|---|---|---|
| *Bacillus subtilis* PCI 219 | 0.05 | 0.10 | 0.10 | 0.025 | ≦0.0008 | 0.10 | ≦0.0008 | 0.05 | 0.20 | 0.013 | 0.013 | 0.05 | 0.05 |
| *Staphylococcus aureus* FDA 209P JC-1 | 0.39 | 0.39 | 0.39 | 0.39 | 0.20 | 0.10 | 0.10 | 0.78 | 0.39 | 0.05 | 0.05 | 0.39 | 0.39 |
| *Staphylococcus aureus* NR 2855 | 0.20 | 3.13 | 1.56 | 0.39 | 0.0065 | 0.78 | 0.05 | 0.78 | 6.25 | 0.20 | 0.10 | 0.39 | 0.20 |
| *Staphylococcus aureus* Smith | 0.20 | 0.39 | 0.20 | 0.20 | 0.0033 | 0.10 | 0.025 | 0.39 | 0.39 | 0.025 | 0.025 | 0.20 | 0.39 |
| *Staphylococcus epidermidis* IFO 12993 | 0.39 | 1.56 | 0.78 | 0.39 | 0.20 | 0.39 | 0.10 | 0.78 | 1.56 | 0.20 | 0.10 | 0.39 | 0.39 |
| *Staphylococcus epidermidis* NR 2942 | 0.39 | 1.56 | 0.78 | 0.39 | 0.0065 | 0.39 | 0.05 | 0.78 | 1.56 | 0.10 | 0.10 | 0.39 | 0.39 |
| *Enterococcus faecalis* NR 2943 | 3.13 | 12.5 | 12.5 | 6.25 | 12.5 | 3.13 | 3.13 | 6.25 | 25 | 1.56 | 1.56 | 6.25 | 3.13 |
| Gram-negative bacteria | | | | | | | | | | | | | |
| *Alcaligenes faecalis* IFO 13111 | 0.39 | 3.13 | 6.25 | 0.78 | 6.25 | 50 | 3.13 | 3.13 | 50 | 6.25 | 6.25 | 6.25 | 0.78 |
| *Citrobacter freundii* IFO 12681 | 0.013 | 0.013 | 0.05 | 0.025 | 0.39 | 0.78 | 0.39 | 0.05 | 0.10 | 0.20 | 0.10 | 1.56 | 0.78 |
| *Enterobacter aerogenes* NR 2945 | 0.013 | 0.013 | 0.05 | 0.025 | 0.0065 | 0.20 | 0.20 | 0.05 | 0.05 | 0.05 | 0.05 | 1.56 | 0.20 |
| *Enterobacter cloacae* NR 2946 | 0.025 | 0.025 | 0.10 | 0.05 | 0.013 | 0.78 | 0.39 | 0.10 | 0.10 | 0.10 | 0.05 | 1.56 | 0.78 |
| *Escherichia coli* NIHJ JC-2 | 0.025 | 0.025 | 0.10 | 0.05 | 0.10 | 0.20 | 0.39 | 0.10 | 0.20 | 0.10 | 0.05 | 1.56 | 0.39 |
| *Escherichia coli* 2630 | 0.013 | 0.025 | 0.025 | 0.013 | ≦0.0008 | 0.10 | — | — | — | 0.025 | 0.013 | 0.39 | 0.20 |
| *Klebsiella pneumoniae* FDA PCI 602 | 0.10 | 0.10 | 0.39 | 0.20 | 3.13 | 3.13 | 0.78 | 0.39 | 1.56 | 0.78 | 0.39 | 6.25 | 0.78 |
| *Bordetella bronchiseptica* ATCC 4617 | 0.20 | 6.25 | 3.13 | 0.39 | 1.56 | 6.25 | 0.78 | 0.78 | 25 | 6.25 | 3.13 | 6.25 | 0.78 |
| *Proteus rettgeri* ATCC 14505 | 0.20 | 0.10 | 0.78 | 0.39 | 1.56 | 12.5 | 0.78 | 0.78 | 1.56 | 1.56 | 0.39 | 3.13 | 0.78 |
| *Proteus vulgaris* OX19 ATCC 6898 | 0.013 | 0.013 | 0.025 | 0.025 | ≦0.0008 | 0.10 | 0.05 | 0.025 | 0.10 | 0.025 | 0.025 | 0.39 | 0.05 |
| *Pseudomonas aeruginosa* A3 | 0.20 | 0.10 | 0.20 | 0.39 | 6.25 | 0.78 | 1.56 | 0.78 | 0.39 | 0.39 | 0.78 | 6.25 | 1.56 |
| *Pseudomonas aeruginosa* NR 2950 | 0.78 | 0.78 | 3.13 | 3.13 | 12.5 | 12.5 | 6.25 | 3.13 | 6.25 | 6.25 | 6.25 | 25 | 3.13 |
| *Pseudomonas stutzeri* IFO 12695 | 0.025 | 0.025 | 0.05 | 0.025 | ≦0.0008 | — | 0.10 | 0.05 | 0.05 | 0.025 | 0.025 | 0.39 | 0.20 |
| *Serratia marcescens* IFO 12648 | 0.10 | 0.10 | 0.20 | 0.10 | 0.78 | 3.13 | 0.39 | 0.39 | 0.39 | 0.78 | 0.39 | 3.13 | 0.39 |
| *Salmonella typhimurium* IFO 12529 | 0.025 | 0.013 | 0.05 | 0.025 | 0.0033 | 0.20 | 0.10 | 0.05 | 0.10 | 0.05 | 0.025 | 1.56 | 0.39 |

| | Compound (Example No.) | | | | | | | | | | | |
|---|---|---|---|---|---|---|---|---|---|---|---|---|
| Aerobic microorganisms | 22 | 24 | 25 | 26 | 27 | 30 | 31 | 32 | 33 | 34 | 35 | 36 |
| Gram-positive bacteria | | | | | | | | | | | | |
| *Bacillus subtilis* PCI 219 | 0.05 | 0.39 | 0.78 | 0.78 | 0.39 | 0.025 | 0.05 | 0.05 | 0.20 | 0.05 | 0.05 | 0.025 |
| *Staphylococcus aureus* FDA 209P JC-1 | 0.20 | 1.56 | 6.25 | 3.13 | 1.56 | 0.05 | 0.39 | 0.20 | 0.20 | 0.20 | 0.39 | 0.39 |
| *Staphylococcus aureus* NR 2855 | 0.39 | 6.25 | 12.5 | 1.56 | 12.5 | 0.39 | 0.78 | 0.39 | 1.56 | 1.56 | 1.56 | 0.10 |
| *Staphylococcus aureus* Smith | 0.20 | 1.56 | 1.56 | 3.13 | 1.56 | 0.05 | 0.20 | 0.10 | 0.20 | 0.20 | 0.39 | 0.10 |
| *Staphylococcus epidermidis* IFO 12993 | 0.39 | 3.13 | 6.25 | 3.13 | 6.25 | 0.20 | 0.39 | 0.39 | 0.78 | 0.78 | 0.78 | 0.20 |
| *Staphylococcus epidermidis* NR 2942 | 0.20 | 3.13 | 6.25 | 3.13 | 6.25 | 0.20 | 0.39 | 0.39 | 0.78 | 0.78 | 0.78 | 0.20 |
| *Enterococcus faecalis* NR 2943 | 3.13 | 25 | 100 | 25 | 50 | 3.13 | 12.5 | 6.25 | 3.13 | 6.25 | 6.25 | 3.13 |
| Gram-negative bacteria | | | | | | | | | | | | |
| *Alcaligenes faecalis* IFO 13111 | 3.13 | 25 | 50 | 12.5 | 50 | 1.56 | 3.13 | 1.56 | 50 | 50 | 25 | 3.13 |
| *Citrobacter freundii* IFO 12681 | 0.10 | 1.56 | 0.78 | 0.78 | 0.20 | 0.013 | 0.05 | 0.10 | 0.20 | 0.20 | 0.20 | 0.20 |
| *Enterobacter aerogenes* NR 2945 | 0.10 | 0.78 | 0.39 | 0.20 | 0.20 | 0.0033 | 0.025 | 0.025 | 0.05 | 0.10 | 0.10 | 0.05 |
| *Enterobacter cloacae* NR 2946 | 0.10 | 3.13 | 0.78 | 0.78 | 0.78 | 0.013 | 0.05 | 0.10 | 0.20 | 0.20 | 0.39 | 0.10 |
| *Escherichia coli* NIHJ JC-2 | 0.10 | 1.56 | 0.78 | 0.78 | 0.78 | 0.013 | 0.05 | 0.10 | 0.20 | 0.20 | 0.10 | 0.10 |
| *Escherichia coli* NR 2630 | 0.025 | 0.78 | 0.39 | 0.20 | — | 0.0065 | 0.025 | 0.025 | 0.10 | 0.10 | 0.10 | 0.05 |
| *Klebsiella pneumoniae* FDA PCI 602 | 0.39 | 6.25 | 3.13 | 3.13 | 3.13 | 0.10 | 0.20 | 0.39 | 0.78 | 0.78 | 1.56 | 0.39 |
| *Bordetella bronchiseptica* ATCC 4617 | 1.56 | 50 | 100 | 12.5 | 25 | 1.56 | 3.13 | 1.56 | 25 | 25 | 12.5 | 0.39 |
| *Proteus rettgeri* ATCC 14505 | 0.78 | 12.5 | 25 | 6.25 | 12.5 | 0.10 | 0.39 | 1.56 | 1.56 | 3.13 | 3.13 | 0.78 |
| *Proteus vulgaris* OX19 ATCC 6898 | 0.0065 | 0.39 | 0.10 | 0.39 | 0.20 | 0.0065 | 0.025 | 0.025 | 0.05 | 0.05 | 0.05 | 0.025 |
| *Pseudomonas aeruginosa* A3 | 1.56 | 3.13 | 3.13 | 6.25 | 3.13 | 0.05 | 0.20 | 0.39 | 0.39 | 0.78 | 1.56 | 0.78 |
| *Pseudomonas aeryginosa* NR 2950 | 6.25 | 25 | 50 | 50 | 25 | 0.20 | 1.56 | 3.13 | 6.25 | 6.25 | 12.5 | 6.25 |
| *Pseudomonas stutzeri* IFO 12695 | 0.10 | — | 0.39 | 0.78 | 0.20 | 0.0033 | 0.025 | 0.10 | — | — | — | 0.10 |
| *Serratia marcescens* IFO 12648 | 0.78 | 6.25 | 3.13 | 1.56 | 3.13 | 0.05 | 0.20 | 0.39 | 0.78 | 0.78 | 1.56 | 0.39 |
| *Salmonella typhimurium* IFO 12529 | 0.10 | 0.78 | 0.20 | 0.78 | 0.39 | 0.0065 | 0.025 | 0.025 | 0.10 | 0.10 | 0.10 | 0.10 |

| | Compound (Example No.) | | | | | | | | | | | |
|---|---|---|---|---|---|---|---|---|---|---|---|---|
| Aerobic microorganisms | 37 | 38 | 39 | 40 | 41 | 42 | 43 | 44 | 45 | 46 | 48 | 49 |
| Gram-positive bacteria | | | | | | | | | | | | |
| *Bacillus subtilis* PCI 219 | ≦0.0008 | ≦0.0008 | 0.025 | 0.10 | 3.13 | 0.05 | 0.10 | 0.05 | 0.39 | 0.05 | 0.05 | 3.13 |
| *Staphylococcus aureus* FDA 209P JC-1 | 0.0016 | 0.39 | 0.39 | 1.56 | 6.25 | 0.39 | 0.78 | 0.78 | 1.56 | 0.78 | 0.39 | 6.25 |
| *Staphylococcus aureus* NR 2855 | ≦0.0008 | 0.20 | 0.78 | 0.78 | 6.25 | 0.39 | 0.78 | 0.39 | 3.13 | 0.39 | 0.39 | 12.5 |
| *Staphylococcus aureus* Smith | ≦0.0008 | 0.10 | 0.39 | 0.78 | 6.25 | 0.39 | 0.39 | 0.39 | 0.78 | 0.39 | 0.20 | 6.25 |
| *Staphylococcus epidermidis* IFO 12993 | 0.025 | 0.39 | 0.39 | 1.56 | 6.25 | 0.39 | 0.39 | 0.78 | 3.13 | 0.78 | 0.39 | 12.5 |
| *Staphylococcus epidermidis* NR 2942 | ≦0.0008 | 0.39 | 0.39 | 0.78 | 12.5 | 0.39 | 0.39 | 0.39 | 3.13 | 0.39 | 0.78 | 12.5 |
| *Enterococcus faecalis* NR 2943 | 3.13 | 12.5 | 12.5 | 12.5 | 100 | 6.25 | 6.25 | 12.5 | 50 | 6.25 | 6.25 | 100 |
| Gram-negative bacteria | | | | | | | | | | | | |
| *Alcaligenes faecalis* IFO 13111 | 12.5 | 6.25 | 6.25 | 6.25 | 50 | 1.56 | 0.78 | 1.56 | 12.5 | 1.56 | 3.13 | 100 |
| *Citrobacter freundii* IFO 12681 | 0.78 | 6.25 | 0.78 | 0.20 | 0.39 | 0.05 | 0.10 | 0.20 | 0.10 | 0.10 | 0.39 | 0.39 |
| *Enterobacter aerogenes* NR 2945 | 0.10 | 3.13 | 0.05 | 0.10 | 0.10 | 0.025 | 0.10 | 0.10 | 0.05 | 0.10 | 0.39 | 0.39 |
| *Enterobacter cloacae* NR 2946 | 0.20 | 6.25 | 0.78 | 0.39 | 0.78 | 0.05 | 0.10 | 0.20 | 0.20 | 0.20 | 0.39 | 0.78 |
| *Escherichia coli* NIHJ JC-2 | 0.10 | 6.25 | 0.78 | 0.39 | 0.78 | 0.05 | 0.10 | 0.20 | 0.20 | 0.10 | 0.39 | 1.56 |
| *Escherichia coli* NR 2630 | ≦0.0008 | 0.39 | 0.025 | 0.20 | 0.39 | 0.025 | 0.05 | 0.05 | 0.10 | 0.05 | 0.10 | 0.39 |
| *Klebsiella pneumoniae* FDA PCI 602 | 3.13 | 25 | 1.56 | 1.56 | 3.13 | 0.39 | 0.39 | 0.39 | 0.39 | 0.78 | 1.56 | 1.56 |
| *Bordetella bronchiseptica* ATCC 4617 | 1.56 | 6.25 | 0.78 | 1.56 | 25 | 0.39 | 0.39 | 0.39 | 12.5 | 0.39 | 6.25 | 50 |
| *Proteus rettgeri* ATCC 14505 | 6.25 | 25 | 3.13 | 3.13 | 3.13 | 0.39 | 0.78 | 1.56 | 0.78 | 1.56 | 3.13 | 3.13 |
| *Proteus vulgaris* OX19 ATCC 6898 | ≦0.0008 | 3.13 | 0.05 | 0.20 | 1.56 | 0.025 | 0.10 | 0.10 | 0.10 | 0.05 | 0.39 | 0.78 |
| *Pseudomonas aeruginosa* A3 | 6.25 | 25 | 3.13 | 1.56 | 3.13 | 0.39 | 0.78 | 0.78 | 0.78 | 1.56 | 3.13 | 3.13 |
| *Pseudomonas aeruginosa* NR 2950 | 25 | 50 | 12.5 | 12.5 | 12.5 | 3.13 | 6.25 | 6.25 | 6.25 | 6.25 | 50 | 50 |
| *Pseudomonas stutzeri* IFO 12695 | 0.013 | 6.25 | — | — | — | 0.10 | — | 0.20 | 0.05 | — | 1.56 | — |

TABLE 1-continued

| Antibacterial spectrum MIC (μg/ml) | | | | | | | | | | | | |
|---|---|---|---|---|---|---|---|---|---|---|---|---|
| Serratia marcescens IFO 12648 | 0.78 | 12.5 | 1.56 | 1.56 | 3.13 | 0.10 | 0.20 | 0.39 | 0.78 | 0.39 | 1.56 | 3.13 |
| Salmonella typhimurium IFO 12529 | 0.20 | 6.25 | 0.20 | 0.39 | 0.78 | 0.025 | 0.10 | 0.20 | 0.10 | 0.10 | 0.39 | 0.39 |

| | Compound (Example No.) | | | | | | | | |
|---|---|---|---|---|---|---|---|---|---|
| Aerobic microorganisms | 50 | 51 | 52 | 53 | 54 | 56 | 59 | 63 | 69 |
| Gram-positive bacteria | | | | | | | | | |
| Bacillus subtilis PCI 219 | 0.0065 | 0.10 | 0.20 | 0.025 | 0.025 | 0.20 | 0.0065 | 0.78 | 0.20 |
| Staphylococcus aureus FDA 209P JC-1 | 0.39 | 0.20 | 0.39 | 0.10 | 0.013 | 0.39 | 0.39 | 0.78 | 1.56 |
| Staphylococcus aureus NR 2855 | 0.39 | 1.56 | 3.13 | 0.10 | 0.20 | 0.78 | 0.10 | 3.13 | 1.56 |
| Staphylococcus aureus Smith | 0.10 | 0.39 | 0.39 | 0.05 | 0.025 | 0.39 | 0.05 | 0.39 | 0.78 |
| Staphylococcus epidermidis IFO 12993 | 0.39 | 0.78 | 1.56 | 0.10 | 0.10 | 0.39 | 0.39 | 1.56 | 1.56 |
| Staphylococcus epidermidis NR 2942 | 0.20 | 0.78 | 1.56 | 0.10 | 0.10 | 0.39 | 0.20 | 0.78 | 1.56 |
| Enterococcus faecalis NR 2943 | 3.13 | 12.5 | 25 | 1.56 | 1.56 | 12.5 | 3.13 | 25 | 12.5 |
| Gram-negative bacteria | | | | | | | | | |
| Alcaligenes faecalis IFO 13111 | 12.5 | 3.13 | 12.5 | 3.13 | 6.25 | 3.13 | 6.25 | 100 | 3.13 |
| Citrobacter freundii IFO 12681 | 3.13 | 0.025 | 0.025 | 0.10 | 0.10 | 0.10 | 1.56 | 0.78 | 0.10 |
| Enterobacter aerogenes NR 2945 | 0.78 | 0.025 | 0.025 | 0.10 | 0.025 | 0.10 | 0.78 | 0.39 | 0.10 |
| Enterobacter cloacae NR 2946 | 1.56 | 0.05 | 0.05 | 0.20 | 0.10 | 0.05 | 0.78 | 1.56 | 0.20 |
| Escherichia coli NIHJ JC-2 | 1.56 | 0.10 | 0.05 | 0.20 | 0.10 | 0.10 | 1.56 | 1.56 | 0.20 |
| Escherichia coli NRD 2630 | 0.20 | 0.025 | 0.025 | 0.05 | 0.025 | 0.0065 | 0.39 | 0.78 | 0.10 |
| Klebsiella pneumoniae FDA PCI 602 | 6.25 | 0.20 | 0.20 | 0.39 | 0.78 | 0.39 | 3.13 | 6.25 | 0.39 |
| Bordetella bronchiseptica ATCC 4617 | 3.13 | 1.56 | 6.25 | 0.78 | 3.13 | 3.13 | 3.13 | 50 | 0.78 |
| Proteus rettgeri ATCC 14505 | 6.25 | 0.20 | 0.20 | 1.56 | 0.78 | 1.56 | 3.13 | 6.25 | 0.78 |
| Proteus vulgaris OX19 ATCC 6898 | 0.39 | 0.025 | 0.025 | 0.10 | 0.013 | 0.013 | 0.20 | 0.39 | 0.05 |
| Pseudomonas aeruginosa A3 | 6.25 | 0.10 | 0.20 | 0.78 | 0.20 | 3.13 | 3.13 | 3.13 | 0.78 |
| Pseudomonas aeruginosa NR 2950 | 25 | 1.56 | 1.56 | 12.5 | 1.56 | 6.25 | 25 | 25 | 6.25 |
| Pseudomonas stutzeri IFO 12695 | — | 0.05 | 0.05 | 0.20 | 0.013 | 0.0033 | 1.56 | 0.39 | 0.20 |
| Serratia marcescens IFO 12648 | 3.13 | 0.10 | 0.20 | 0.78 | 0.39 | 0.78 | 3.13 | 3.13 | 0.20 |
| Salmonella typhimurium IFO 12529 | 0.78 | 0.025 | 0.025 | 0.10 | 0.025 | 0.05 | 1.56 | 0.78 | 0.10 |

TABLE 2

| Antibacterial spectrum MIC (μg/ml) | | |
|---|---|---|
| | Compound (Example No.) | |
| Anaerobic microorganisms | 5 | 30 |
| Bacteroides fragilis ATCC 23745 | 0.78 | 0.20 |
| Bacteroides fragilis NR 2579 | 3.13 | 1.56 |
| Bacteroides fragilis NR 2582 | 0.78 | 0.39 |
| Bacteroides fragilis NR 2583 | 0.39 | 0.10 |
| Bacteroides fragilis NR 2584 | 0.78 | 0.78 |
| Bacteroides distasonis NR 2578 | 0.78 | 0.78 |
| Bacteroides thetaiotaomicron NR 2588 | 1.56 | 0.78 |
| Bifidobacterium adolescentis ATCC 15703 | 0.39 | 0.10 |
| Clostridium botulinum NR 2611 | 0.10 | 0.013 |
| Clostridium perfringens NR 2612 | 0.39 | 0.10 |
| Clostridium moniliforme ATCC 25546 | 0.78 | 0.10 |
| Fusobacterium varium ATCC 8501 | 12.5 | — |
| Peptococcus prevotii ATCC 9321 | 1.56 | 0.39 |
| Peptococcus variabilis ATCC 14955 | 0.78 | 0.20 |
| Peptostreptococcus anaerobius NR 2743 | 0.39 | 0.013 |
| Propionibacterium acnes ATCC 11828 | 0.78 | 0.78 |
| Mycoplasma | | |
| Myoplasma hominis NR 2952 | 0.10 | 0.10 |

2. In Vivo Therapeutic Efficacy

The in vivo antibacterial activities of pyrido[3,2,1-ij]-1,3,4-benzoxadiazine derivatives prepared by Example 5, Example 30, Example 65 and Example 66 as mentioned below were tested against lethal infection of *Escherichia coli* ML4707, *Pseudomonas aeruginosa* 4au542 and *Streptococcus pneumoniae* 6-001. ICR mice weighing about 20 g were infected by intraperitoneal injection of a corresponding bacterial suspension. The test compounds were administered orally or subcutaneously at the time of injection. The mortality was observed for 5 days. The respective 50% effective dose ($ED_{50}$, mg/kg) which protects 50% of the animals from death caused by infection, is shown in Table 3.

TABLE 3

| In vivo Antibacterial Activities Against Systemic Infection in Mice ($ED_{50}$, mg/kg) | | | | |
|---|---|---|---|---|
| | Bacterium | | | |
| | Escherichia coli ML4707 | | Pseudomonas aeruginosa 4au542 | Streptococcus pneumoniae 6-001 |
| Compound | s.c. | p.o. | p.o. | p.o. |
| Example 5 | 0.06 | 0.11 | 13.4 | 10.3 |
| Example 30 | 0.10 | 0.62 | 57.0 | 65.9 |
| Example 65 | — | 1.12 | — | — |
| Example 66 | — | 0.51 | — | — |

3. Acute Toxicity

The respective $LD_{50}$ values of the compounds obtained in Examples 5, 6, 7, 16, 17, 18, 30, 36 and 56 as mentioned below are more than 2000 mg/kg. The acute toxicity of these compounds was examined by oral administration in ICR mice.

The compounds provided according to the present invention exhibit a broad antimicrobial spectrum against gram-positive, gram-negative bacteria and Mycoplasma, in particular against those which are resistant to various antibiotics, such as penicillins, cephalosporins, aminoglycosides, tetracyclins, and the like.

Moreover, the compounds provided according to the present invention have low toxicity, and a potent and broad antimicrobial efficacy. The protective effects of the compounds of the present invention on systemic bacterial infections in mice are greater than those of synthetic antibacterial agents which are commercially available. Therefore, the compounds of the present invention can be effectively utilized for the prevention or treatment of diseases caused by gram-positive and gram-negative bacteria, and bacterioid microorganisms in human beings or animals.

For example, diseases caused by the following microorganisms, or by mixtures of the following microorganisms can be treated and/or prevented: Staphylococcus, Streptococcus, Aerococcus, Enterococcus, Micrococcus, Lactobacillus, Bifidobacterium, Clostridium, Eubacterium, Peptococcus, Peptostreptococcus, Propionibacterium, Escherichia, Citrobacter, Campylobacter, Enterobacter, Klebsiella, Proteus, Pseudomonas, Serratia, Salmonella, Shigella, Vibrio, Aeromonas, Haemophilus, Neisseria, Acinetobacter, Alcaligenes, Bordetella, Bacteroides, Fusobacterium, Mycoplasma and other microorganisms.

The present invention further relates to the pharmaceutical compositions containing one or more compounds of the present invention.

The compounds of the present invention can be administered orally or non-orally to human beings or animals by various conventional administration methods.

Moreover, the compounds according to the present invention are used singly or formulated with auxiliaries, liquid diluents, binders, lubricants, humectants, etc., for example, in the form of general medicinal compositions such as tablets, granulars, sugar coating tablets, powder, capsules, gels, dry syrup, syrup, ampules, suspension, liquid, emulsion, ointments, paste, cream, suppositories, and the like.

Furthermore, dissolution delaying agents, absorption accelerating agents, surface active agents, and the like can be used as other additives for formulation, i.e., any forms which are pharmaceutically acceptable can be employed.

The compounds according to the present invention can be used as alone or mixture of two or more different kinds of compounds and the amount of the compounds is about 0.1 to 99.5%, preferably 0.5 to 95% based on the weight of the all medicinal composition.

The medical composition according to the present invention may be formulated in a combination of the compound of the present invention or the mixture thereof with other conventional compounds which are pharmaceutically active.

A dosage per day to a patient of the novel compound according to the present invention may be varied depending upon an individual man, kinds of animals, weights thereof and a state to be remedied, but generally is in the range of 0.5 to 500 mg per 1 kg of weight, preferably about 1 to 300 mg.

The following examples illustrate the preferred methods for the preparation of the compounds of the present invention. Unless otherwise indicated, the examples were carried out as written.

PREPARATION OF STARTING MATERIALS

Reference Example

Preparation of diethyl N-(3,4-difluoro-2-hydroxyphenyl)aminomethylenemalonate (a) A solution of 2,3-difluoro-6-nitrophenol (500 mg) in methanol (7 ml) was hydrogenated over 5% Pd/C (60 mg) for 6 hours. The reaction mixture was filtered under nitrogen stream and the filtrate was evaporated under reduced pressure to give 414 mg of crude 2-amino-5,6-difluorophenol.

(b) A mixture of the above amine (414 mg) and diethyl ethoxymethylenemalonate (618 mg) was heated at 130° C. under nitrogen atmosphere for 5 minutes. The resulting crystalline residue was triturated with ethanol and filtered to give 590 mg of diethyl N-(3,4-difluoro-2-hydroxyphenyl)-aminomethylenemalonate, mp 178°–180° C.; MS m/z 315 (M+). Additional 59 mg of the crystals were obtained after silica gel column chromatography of the mother liquid using CHCl$_3$/acetone (20:1) as the eluent.

Preparation of ethyl 8-benzyloxy-6,7-difluoro-4-hydroxy-3-quinolinecarboxylate (Route 1)

(c) To a mixture of diethyl N-(3,4-difluoro-2-hydroxyphenyl)aminomethylenemalonate (80 mg) and anhydrous potassium carbonate (70 mg) in dry dimethylformamide (1.5 ml) was added benzyl bromide (30 μl). The mixture was stirred at room temperature for 2 hours. After removal of the solvent under reduced pressure, the residue was dissolved in dichloromethane and the precipitate was filtered off. The filtrate was washed with water, dried over anhydrous sodium sulfate and evaporated. The crystalline residue was washed with n-hexane and recrystallized from methanol to give diethyl N-(2-benzyloxy-3,4-difluorophenyl)-aminomethylenemalonate (90 mg), mp 87° C.; MS m/z 405 (M+).

(d) A solution of the above malonate (280 mg) in diphenyl ether (2.8 ml) was heated at 250° C. for 30 minutes under nitrogen atmosphere. After cooling the reaction mixture, the ethanol generated in reaction medium was removed under reduced pressure. The dark brown solution was applied onto a column of silica gel (10 g) followed by successive elution with benzene, dichloromethane and dichloromethane/acetone (30:1). The pure fractions were combined and the solvent was removed under reduced pressure to give the crystalline residue. The residue was washed with a mixture of n-hexane and ethyl acetate to give 90 mg of ethyl 8-benzyloxy-6,7-difluoro-4-hydroxy-3-quinolinecarboxylate. An analytical sample, mp 200°–201° C.; MS m/z 359 (M+), was prepared by recrystallization from methanol.

Preparation of ethyl 8-benzyloxy-6,7-difluoro-4-hydroxy-3-quinolinecarboxylate (Route 2)

To a stirred solution of ethyl 6,7-difluoro-4,8-dihydroxy-3-quinolinecarboxylate (300 mg) in dry dimethylformamide (6 ml), was added anhydrous potassium carbonate (308 mg) and then benzyl chloride (145 μl). The mixture was stirred at 55°–65° C. for 11 hours. The reaction mixture was diluted with water (30 ml) and extracted with chloroform. The extract was dried over anhydrous sodium sulfate and concentrated under reduced pressure. The residue was chromatographed on silica gel (7 g) using acetone/chloroform (1:20) as an eluent to give 113 mg of ethyl 8-benzyloxy-6,7-difluoro-4-hydroxy-3-quinolinecarboxylate, mp 200°–201° C.; MS m/z 359 (M+), after recrystallization from methanol.

Preparation of ethyl 8-benzyloxy-6,7-difluoro-1-(formylmethylamino)-4-oxo-1,4-dihydro-3-quinolinecarboxylate (e) After a mixture of ethyl 8-benzyloxy-6,7-difluoro-4-hydroxy-3-quinolinecarboxylate (410 mg) and anhydrous potassium carbonate (315 mg) in dry dimethylformamide (10 ml) was stirred at room temperature for 3 hours, O-(2,4-dinitrophenyl)hydroxylamine (260 mg) was added. The mixture was stirred at room temperature for further 6.5 hours. After removal of the solvent under reduced pressure, water (12 ml) was added to the residue, and the mixture was stirred at room temperature for 3 hours. The precipitate was collected by filtration and washed with cold water and then with ether to give 405 mg of ethyl 1-amino-8-benzyloxy-6,7-difluoro-4-oxo-1,4-dihydro-3-quinolinecarboxylate. An analytical sample, mp 143°–144° C.; MS m/z 374 (M+), was prepared by recrystallization from methanol.

(f) 98% Formic acid (0.60 ml) was added to acetic anhydride (1.51 ml) at 0° C. The mixture was stirred at 0° C. for 15 minutes, at 50° C. for 15 minutes, and then cooled to 0° C. To this solution was added dropwise a solution of the above amine (400 mg) in 98% formic acid (2.1 ml). The mixture was stirred at room temperature for 2 days. The reaction mixture was evaporated under reduced pressure to give the crystalline residue, which was recrystallized from ethanol to give 410 mg of ethyl 8-benzyloxy-6,7-difluoro-1-(formylamino)-4-oxo-1,4-dihydro-3-quinolinecarboxylate, mp 188°–190° C.; MS m/z 402 (M+).

(g) A mixture of the above formamide (400 mg), anhydrous potassium carbonate (275 mg) and anhydrous dimethylformamide (17 ml) was stirred at room temperature for 1.5 hours. Methyl iodide (0.19 ml) was added to the mixture and stirring was continued for 2.5 hours. The solvent was removed under reduced pressure and the residue was partitioned between chloroform and water. The organic layer was dried over anhydrous sodium sulfate and concentrated to dryness under reduced pressure. The residue was recrystallized from ethanol to give 335 mg of ethyl 8-benzyloxy-6,7-difluoro-1-(formylmethylamino)-4-oxo-1,4-dihydro-3-quinolinecarboxylate, mp 180°–181° C.; MS m/z 416 (M+).

Preparation of 6,7-difluoro-8-hydroxy-1-(methylamino)-4-oxo-1,4-dihydro-3-quinolinecarboxylic acid (h) Ethyl 8-benzyloxy-6,7-difluoro-1-(formylmethylamino)-4-oxo-1,4-dihydro-3-quinolinecarboxylate (330 mg) was hydrogenated over 5% Pd/C (50 mg) in chloroform (14 ml) for 4 hours. The reaction mixture was diluted with methanol (14 ml) and filtered. The filtered cake was washed with chloroform/methanol (1:1). The combined filtrate was evaporated and the residue was recrystallized from ethanol to give 239 mg of ethyl 6,7-difluoro-1-(formylmethylamino)-8-hydroxy-4-oxo-1,4-dihydro-3-quinolinecarboxylate, mp 221°–225° C. (dec.); MS m/z 326 (M+).

(i) A mixture of the above ester (210 mg) and 0.5N sodium hydroxide (5.2 ml) was heated at 100° C. for 2 hours under nitrogen atmosphere. The reaction mixture was acidified with acetic acid (0.16 ml). The precipitate which separated out was filtered, washed with water and dried under reduced pressure to give 168 mg of 6,7-difluoro-8-hydroxy-1-(methylamino)-4-oxo-1,4-dihydro-3-quinolinecarboxylic acid. An analytical sample, mp 248°–250° C. (dec.); MS m/z 270 (M+), was prepared by recrystallization from ethanol.

EXAMPLE 1

Preparation of 9,10-difluoro-3-methyl-7-oxo-2,3-dihydro-7H-pyrido[3,2,1-ij]-1,3,4-benzoxadiazine-6-carboxylic acid A mixture of 6,7-difluoro-8-hydroxy-1-(methylamino)-4-oxo-1,4-dihydro-3-quinolinecarboxylic acid (105 mg) obtained in Reference example (i), paraformaldehyde (150 mg) and dry dioxane (5 ml) was heated at 100° C. for 3 hours under nitrogen atmosphere. After removal of the solvent under reduced pressure dimethylformamide (20 ml) was added to the residue and the mixture was stirred for 20 minutes and then filtered. The filtered cake was washed with dimethylformamide and the combined filtrate was evaporated under reduced pressure. The residue was triturated with water and filtered to give 97 mg of 9,10-difluoro-3-methyl-7-oxo-2,3-dihydro-7H-pyrido[3,2,1-ij]-1,3,4-benzoxadiazine-6-carboxylic acid. An analytical sample, mp 290°–292° C. (dec.); MS m/z 282 (M+) was prepared by recrystallization from dimethylformamide.

EXAMPLE 2

Preparation of 9,10-difluoro-2,3-dimethyl-7-oxo-2,3-dihydro-7H-pyrido[3,2,1-ij]-1,3,4-benzoxadiazine-6-carboxylic acid A mixture of 6,7-difluoro-8-hydroxy-1-(methylamino)-4-oxo-1,4-dihydro-3-quinolinecarboxylic acid (50 mg) obtained in Reference example (i), 90% acetaldehyde (1 ml) and dioxane (5 ml) was heated at 100° C. for 3 hours under nitrogen atmosphere. The reaction mixture was evaporated under reduced pressure to give 52 mg of 9,10-difluoro-2,3-dimethyl-7-oxo-2,3-dihydro-7H-pyrido[3,2,1-ij]-1,3,4-benzoxadiazine-6-carboxylic acid, mp 285°–289° C.; MS m/z 296 (M+).

EXAMPLE 3

Preparation of 9,10-difluoro-2-(hydroxymethyl)-3-methyl-7-oxo-2,3-dihydro-7H-pyrido[3,2,1-ij]-1,3,4-benzoxadiazine-6-carboxylic acid A suspension of 6,7-difluoro-8-hydroxy-1-(methylamino)-4-oxo-1,4-dihydro-3-quinolinecarboxylic acid (50 mg) obtained in Reference example (i), glycolaldehyde diethylacetal (45 μl) and pyridinium p-toluenesufonate (7 mg) in dry dioxane (2 ml) was heated at 110° C. for 5 hours under nitrogen atmosphere. After the solvent was removed under reduced pressure, the crystalline residue was washed with water and methanol to give 52 mg of 9,10-difluoro-2-(hydroxymethyl)-3-methyl-7-oxo-2,3-dihydro-7H-pyrido-[3,2,1-ij]-1,3,4-benzoxadiazine-6-carboxylic acid, mp 254°–258° C. (dec.); MS m/z 312 (M+).

EXAMPLE 4

Preparation of 9,10-difluoro-2-[(dimethylamino)methyl]-3-methyl-7-oxo-2,3-dihydro-7H-pyrido[3,2,1-ij]-1,3,4-benzoxadiazine-6-carboxylic acid p-toluenesulfonate A suspension of 6,7-difluoro-8-hydroxy-1-(methylamino)-4-oxo-1,4-dihydro-3-quinolinecarboxylic acid (50 mg) obtained in Reference example (i), dimethylaminoacetaldehyde dimethylacetal (37 mg) and p-toluenesulfonic acid monohydrate (53 mg) in dry dioxane (2 ml) was heated at 110° C. for 17 hours under nitrogen atmosphere. After the solvent was removed under reduced pressure, the residue was recrystallized from methanol to give 61 mg of 9,10-difluoro-2-[(dimethylamino)methyl]-3-methyl-7-oxo-2,3-dihydro-7H-pyrido[3,2,1-ij]-1,3,4-benzoxadiazine-6-carboxylic acid p-toluenesulfonate, mp 232°–236° C. (dec.); FAB-MS m/z 340 (MH+).

EXAMPLE 5

Preparation of 9-fluoro-3-methyl-10-(4-methyl-1-piperazinyl)-7-oxo-2,3-dihydro-7H-pyrido[3,2,1-ij]-1,3,4-benzoxadiazine-6-carboxylic acid A mixture of 9,10-difluoro-3-methyl-7-oxo-2,3-dihydro-7H-pyrido[3,2,1-ij]-1,3,4-benzoxadiazine-6-carboxylic acid (30 mg) obtained in Example 1, N-methylpiperazine (47 μl) and dry pyridine (3 ml) was heated at 100°–110° C. for 9 hours under nitrogen atmosphere. Pyridine was removed under reduced pressure and the residue was recrystallized from methanol to give 23 mg of 9-fluoro-3-methyl-10-(4-methyl-1-piperazinyl)-7-oxo-2,3-dihydro-7H-pyrido[3,2,1-ij]-1,3,4-benzoxadiazine-6-carboxylic acid, mp 268°–269° C. (dec.); MS m/z 362 (M+).

The following compounds were obtained according to a manner analogous to that of Example 5:

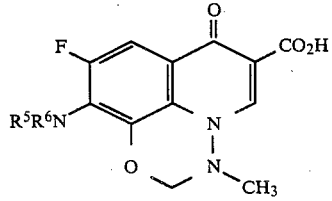

| Example No. | $R^5R^6N-$ | Melting point °C. | Recrystallization solvent | MS m/z |
|---|---|---|---|---|
| 6 | HN⌒N— (piperazinyl) | 240~245 (dec.) | MeOH | 349 (MH+)* |
| 7 | HN⌒N— with CH3 | 237~239 (dec.) | MeOH/CHCl3 | 362 (M+) |
| 8 | HN⌒N— with Ph | 256~259 (dec.) | DMF | 425 (MH+)* |
| 9 | O⌒N— (morpholinyl) | >300 | EtOH/CHCl3 | 349 (M+) |
| 10 | O⌒N— with 2 CH3 | >300 | DMF | 377 (M+) |
| 11 | S⌒N— (thiomorpholinyl) | >300 (dec.) | DMF | 365 (M+) |
| 12 | H2NCH2-piperidinyl-N— | 238~242 (dec.) | MeOH | 377 (MH+)* |
| 13 | HO-piperidinyl-N— | 256~258 | MeOH/CHCl3 | 363 (M+) |

-continued

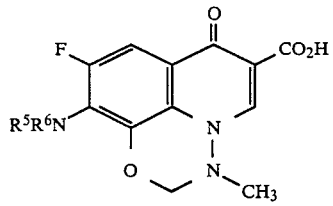

| Example No. | R⁵R⁶N— | Melting point °C. | Recrystallization solvent | MS m/z |
|---|---|---|---|---|
| 14 | pyrrol-1-yl-piperidin-1-yl | 272~274 (dec.) | EtOH | 413 (MH$^+$)* |
| 15 | 4-(2-hydroxyethyl)piperazin-1-yl | 270~275 | H$_2$O | 393 (MH$^+$)* |
| 16 | 1,4-diazepan-1-yl (HN-(CH$_2$)-N—) | 243~246 | MeOH/CHCl$_3$ | 362 (M$^+$) |
| 17 | 3-(methylaminomethyl)pyrrolidin-1-yl (CH$_3$NH-CH$_2$-) | 242~244 (dec.) | DMF | 377 (MH$^+$)* |
| 18 | 3-(ethylaminomethyl)pyrrolidin-1-yl (C$_2$H$_5$NH-CH$_2$-) | 251~252 (dec.) | EtOH | 391 (MH$^+$)* |
| 19 | 3-(acetylaminomethyl)pyrrolidin-1-yl (AcNH-CH$_2$-) | 239~241 (dec.) | EtOH | 405 (MH$^+$)* |
| 20 | (CH$_3$)$_2$N-CH$_2$CH$_2$-N(CH$_3$)— | 256~258 (dec.) | EtOH | 365 (MH$^+$)* |
| 21 | 3-hydroxypyrrolidin-1-yl | 284~286 (dec.) | DMF | 350 (MH$^+$)* |
| 22 | 2-methylimidazol-1-yl (CH$_3$-) | 280~284 (dec.) | MeOH/CHCl$_3$/Et$_2$O | 345 (MH$^+$)* |

-continued

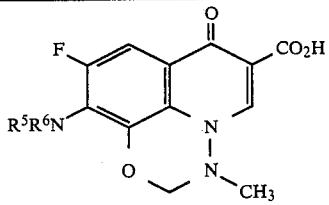

| Example No. | R⁵R⁶N— | Melting point °C. | Recrystallization solvent | MS m/z |
|---|---|---|---|---|
| 23 | CH₃NH-CH₂- (3-pyrrolidinyl, N-CH₃) | 220~222 (dec.) | EtOH | 391 (MH⁺)* |

*FAB—MS

EXAMPLE 24

Preparation of 9-fluoro-3-methyl-7-oxo-10-(3-oxo-1-piperazinyl)-2,3-dihydro-7H-pyrido[3,2,1-ij]-1,3,4-benzoxadiazine-6-carboxylic acid A mixture of 9,10-difluoro-3-methyl-7-oxo-2,3-dihydro-7H-pyrido[3,2,1-ij]-1,3,4-benzoxadiazine-6-carboxylic acid (40 mg) obtained in Example 1, 2-piperazinone (31.1 mg), 1,4-diazabicyclo[2.2.2]octane (31.8 mg) and dry dimethylsulfoxide (1 ml) was heated at 130° C. for 28.5 hours under nitrogen atmosphere. The solvent was removed under reduced pressure. The residue was purified by preparative TLC (Silica gel: CHCl₃/MeOH, 10:1.5) and recrystallized from a mixture of dichloromethane and methanol to give 6.3 mg of 9-fluoro-3-methyl-7-oxo-10-(3-oxo-1-piperazinyl)-2,3-dihydro-7H-pyrido[3,2,1-ij]-1,3,4-benzoxadiazine-6-carboxylic acid, mp >300° C.; FAB-MS m/z 363 (MH⁺).

The following compounds were prepared from the compounds described in Example 2, 3 and 4 according to a manner analogous to that of Example 5:

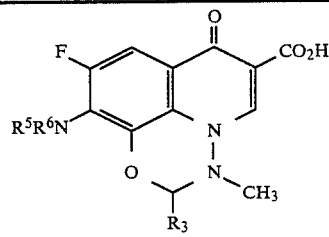

| Example No. | R⁵R⁶N— | R₃ | Melting point °C. | Recrystallization solvent | MS m/z |
|---|---|---|---|---|---|
| 25 | HN⌒N— (piperazinyl) | CH₃ | 240~242 (dec.) | MeOH | 362 (M⁺) |
| 26 | CH₃N⌒N— (4-methylpiperazinyl) | CH₃ | 203~206 | EtOH | 376 (M⁺) |
| 27 | CH₃N⌒N— | CH₂OH | 229~231 (dec.) | MeOH | 393 (MH⁺)* |
| 28 | CH₃N⌒N— | CH₂N(CH₃)₂ | 210~212 | MeOH | 420 (MH⁺)* |

*FAB—MS

EXAMPLE 29

Preparation of 10-[3-(benzyloxycarbonylamino)-1-pyrrolidinyl]-9-fluoro-3-methyl-7-oxo-2,3-dihydro-7H-pyrido-[3,2,1-ij]-1,3,4-benzoxadiazine-6-carboxylic acid A mixture of 9,10-difluoro-3-methyl-7-oxo-2,3-dihydro-7H-pyrido[3,2,1-ij]-1,3,4-benzoxadiazine-6-carboxylic acid (28 mg) obtained in Example 1, 3-(benzyloxycarbonylamino)-pyrrolidine (94 mg) and dry pyridine (3 ml) was heated at 100° C. for 3 hours under nitrogen atmosphere. Pyridine was removed under reduced pressure and the residue was recrystallized from methanol to give 36 mg of 10-[3-(benzyloxycarbonylamino)-1-pyrrolidinyl]-9-fluoro-3-methyl-7-oxo-2,3-dihydro-7H-pyrido[3,2,1-ij]-1,3,4-benzoxadiazine-6-carboxylic acid, mp 227°–230° C.; MS m/z 482 (M+).

EXAMPLE 30

Preparation of 10-(3-amino-1-pyrrolidinyl)-9-fluoro-3-methyl-7-oxo-2,3-dihydro-7H-pyrido[3,2,1-ij]-1,3,4-benzoxadiazine-6-carboxylic acid 10-[3-(benzyloxycarbonylamino)-1-pyrrolidinyl]-9-fluoro-3-methyl-7-oxo-2,3-dihydro-7H-pyrido[3,2,1-ij]-1,3,4-benzoxadiazine-6-carboxylic acid (30 mg) obtained in Example 29 was hydrogenated over 5% Pd/C (10 mg) in dimethylformamide (2 ml) for 4.5 hours. After removal of the catalyst by filtration the filtrate was concentrated under reduced pressure. The residue was recrystallized from methanol to give 16 mg of 10-(3-amino-1-pyrrolidinyl)-9-fluoro-3-methyl-7-oxo-2,3-dihydro-7H-pyrido[3,2,1-ij]-1,3,4-benzoxadiazine-6-carboxylic acid, mp 230°–234° C. (dec.); MS m/z 348 (M+).

The following compounds were obtained according to a manner analogous to that of Examples 29 and 30:

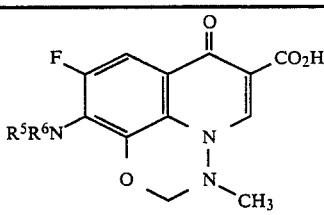

| Example No. | $R^5R^6N-$ | Melting point °C. | Recrystallization solvent | MS m/z |
|---|---|---|---|---|
| 31 | CH$_3$NH–[pyrrolidine]–N– | 286~288 (dec.) | H$_2$O | 363 (MH+)* |
| 32 | C$_2$H$_5$NH–[pyrrolidine]–N– | 269~273 (dec.) | MeOH | 377 (MH+)* |
| 33 | H$_2$N–[piperidine]–N– | 240~245 (dec.) | MeOH | 363 (MH+)* |
| 34 | CH$_3$NH–[piperidine]–N– | 262~265 (dec.) | MeOH | 377 (MH+)* |
| 35 | C$_2$H$_5$NH–[piperidine]–N– | 252~256 (dec.) | EtOH | 390 (M+) |

*FAB—MS

EXAMPLE 36

Preparation of 10-(3,4-dimethyl-1-piperazinyl)-9-fluoro-3-methyl-7-oxo-2,3-dihydro-7H-pyrido[3,2,1-ij]-1,3,4-benzoxadiazine-6-carboxylic acid A mixture of 9-fluoro-3-methyl-10-(3-methyl-1-piperazinyl)-7-oxo-2,3-dihydro-7H-pyrido[3,2,1-ij]-1,3,4-benzoxadiazine-6-carboxylic acid (60 mg) obtained in Example 7, 98% formic acid (1 ml) and 35% formalin (1 ml) was stirred at 100°–110° C. After heating for 2 hours, the mixture was evaporated under reduced pressure. The residue was dissolved in water, neutralized with 1N sodium hydroxide and extracted with chloroform. The extract was washed with water and dried over anhydrous sodium sulfate. After the solvent was removed under reduced pressure the crystalline residue was recrystallized from methanol to give 43 mg of 10-(3,4-dimethyl-1-piperazinyl)-9-fluoro-3-methyl-7-oxo-2,3-dihydro-7H-pyrido[3,2,1-ij]-1,3,4-benzoxadiazine-6-carboxylic acid, mp 257°–259° C.; FAB-MS m/z 377 (MH+).

EXAMPLE 37

Preparation of 9-fluoro-10-(3-methoxy-1-pyrrolidinyl)-3-methyl-7-oxo-2,3-dihydro-7H-pyrido[3,2,1-ij]-1,3,4-benzoxadiazine-6-carboxylic acid To a suspension of 9-fluoro-10-(3-hydroxy-1-pyrrolidinyl)-3-methyl-7-oxo-2,3-dihydro-7H-pyrido[3,2,1-ij]-1,3,4-benzoxadiazine-6-carboxylic acid (100 mg) obtained in Example 21 in dry dimethylformamide (10 ml) was added 60% sodium hydride in oil (30 mg) and methyl iodide (40 μl). After stirring the mixture at room temperature for 2 hours, additional 60% sodium hydride (30 mg) and methyl iodide (40 μl) were added, and the mixture was stirred at 45° C. for 3 hours. The solvent was then removed under reduced pressure. To the residue was added cold water (2 ml) and 0.5N sodium hydroxide (2.3 ml) and the resulting suspension was heated at 100° C. for 2 hours. The reaction mixture was then cooled to room temperature, neutralized with acetic acid and diluted with water. The mixture was extracted with chloroform, and the extract was washed with water, dried over anhydrous sodium sulfate and concentrated under reduced pressure to give the crystalline residue, which was chromatographed on silica gel using acetone/chloroform (1:9) as an eluent. 42 mg of 9-fluoro-10-(3-methoxy-1-pyrrolidinyl)-3-methyl-7-oxo-2,3-dihydro-7H-pyrido[3,2,1-ij]-1,3,4-benzoxadiazine-6-carboxylic acid, mp 233°–234° C.; FAB-MS m/z 364 (MH+), was obtained after recrystallization from methanol.

EXAMPLE 38

Preparation of 9-fluoro-10-(4-methoxy-1-piperidyl)-3-methyl-7-oxo-2,3-dihydro-7H-pyrido[3,2,1-ij]-1,3,4-benzoxadiazine-6-carboxylic acid 9-Fluoro-10-(4-methoxy-1-piperidyl)-3-methyl-7-oxo-2,3-dihydro-7H-pyrido[3,2,1-ij]-1,3,4-benzoxadiazine-6-carboxylic acid was prepared from 9-fluoro-10-(4-hydroxy-1-piperidyl)-3-methyl-7-oxo-2,3-dihydro-7H-pyrido[3,2,1-ij]-1,3,4-benzoxadiazine-6-carboxylic acid obtained in Example 13 analogously to Example 37, and was obtained as crystals, mp. 229°–233° C. (dec.); MS m/z 377 (M+), after recrystallization from chloroform/n-hexane.

EXAMPLE 39

Preparation of 10-(1,1-dioxide-4-thiomorpholinyl)-9-fluoro-3-methyl-7-oxo-2,3-dihydro-7H-pyrido[3,2,1-ij]-1,3,4-benzoxadiazine-6-carboxylic acid To a suspension of 9-fluoro-3-methyl-7-oxo-10-(4-thiomorpholinyl)-2,3-dihydro-7H-pyrido[3,2,1-ij]-1,3,4-benzoxadiazine-6-carboxylic acid (50 mg) obtained in Example 11 in dichloromethane (5 ml) was added m-chloroperbenzoic acid (70% purity, 74 mg). The mixture was stirred at room temperature for 18 hours. The solvent was then removed under reduced pressure. The residue was washed with ether, dichloromethane and a mixture of chloroform and methanol, and recrystallized from dimethylformamide to give 22 mg of 10-(1,1-dioxide-4-thiomorpholinyl)-9-fluoro-3-methyl-7-oxo-2,3-dihydro-7H-pyrido[3,2,1-ij]-1,3,4-benzoxadiazine-6-carboxylic acid, mp >300° C.; MS m/z 397 (M+).

EXAMPLE 40

Preparation of 9-fluoro-3-methyl-7-oxo-10-[4-(2-oxo-n-propyl)-1-piperazinyl]-2,3-dihydro-7H-pyrido[3,2,1-ij]-1,3,4-benzoxadiazine-6-carboxylic acid A mixture of 9-fluoro-3-methyl-7-oxo-10-(1-piperazinyl)-2,3-dihydro-7H-pyrido[3,2,1-ij]-1,3,4-benzoxadiazine-6-carboxylic acid (50 mg) obtained in Example 6, chloroacetone (17 μl), triethylamine (40 μl) and dry dimethylformamide (1 ml) was heated at 80° C. for 3.5 hours. The volatile components were then removed under reduced pressure and the residue was suspended in water. The precipitate was collected by filtration and recrystallized from a mixture of dichloromethane and methanol to give 32 mg of 9-fluoro-3-methyl-7-oxo-10-[4-(2-oxo-n-propyl)-1-piperazinyl]-2,3-dihydro-7H-pyrido[3,2,1-ij]-1,3,4-benzoxadiazine-6-carboxylic acid, mp 225°–229° C. (dec.), FAB-MS m/z 405 (MH+).

The following compounds were obtained according to a manner analogous to that of Example 40.

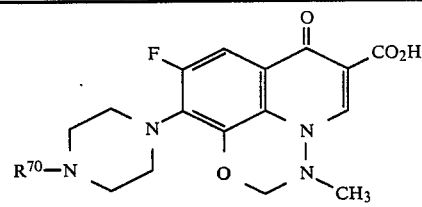

| Example No. | R70 | Melting point °C. | Recrystallization solvent | FAB-MS m/z |
| --- | --- | --- | --- | --- |
| 41 | ⌬—COCH2— | 223~226 (dec.) | DMF | 467 (MH+) |
| 42 | CH3CH2— | 273~275 (dec.) | EtOH | 377 (MH+) |

-continued

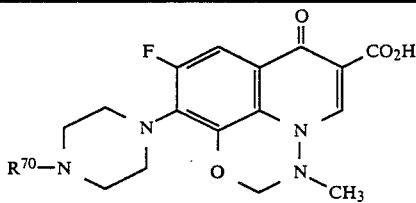

| Example No. | R[70] | Melting point °C. | Recrystallization solvent | FAB-MS m/z |
|---|---|---|---|---|
| 43 | $CH_3CH_2CH_2-$ | 255~257 (dec.) | EtOH | 391 (MH+) |
| 44 | $FCH_2CH_2-$ | 257~259 (dec.) | EtOH | 395 (MH+) |
| 45 | $HO_2CHH_2-$ | 256~259 (dec.) | $H_2O$ | 407 (MH+) |
| 46 | $CH_2=CHCH_2-$ | 236~238 (dec.) | MeOH | 389 (MH+) |
| 47 |  | 275~276 (dec.) | EtOH | 484 (MH+) |

EXAMPLE 48

Preparation of 10-[3-[(ethylmethylamino)methyl]-1-pyrrolidinyl]-9-fluoro-3-methyl-7-oxo-2,3-dihydro-7H-pyrido-[3,2,1-ij]-1,3,4-benzoxadiazine-6-carboxylic acid 10-[3-[(ethylmethylamino)methyl]-1-pyrrolidinyl]-9-fluoro-3-methyl-7-oxo-2,3-dihydro-7H-pyrido[3,2,1-ij]-1,3,4-benzoxadiazine-6-carboxylic acid was prepared from 9-fluoro-3-methyl-10-[3-[(methylamino)methyl]-1-pyrrolidinyl]-7-oxo-2,3-dihydro-7H-pyrido[3,2,1-ij]-1,3,4-benzoxadiazine-6-carboxylic acid obtained in Example 17 and ethyl iodide analogously to Example 40, and was obtained as crystals, mp 210°-225° C. (dec.); FAB-MS m/z 405 (MH+) after recrystallization from a mixture of chloroform, methanol and n-hexane.

EXAMPLE 49

Preparation of 10-[4-(3-carboxypropionyl)-1-piperazinyl]-9-fluoro-3-methyl-7-oxo-2,3-dihydro-7H-pyrido[3,2,1-ij]-1,3,4-benzoxadiazine-6-carboxylic acid A mixture of 9-fluoro-3-methyl-7-oxo-10-(1-piperazinyl)-2,3-dihydro-7H-pyrido[3,2,1-ij]-1,3,4-benzoxadiazine-6-carboxylic acid (50 mg) obtained in Example 6, succinic anhydride (21.6 mg), triethylamine (40 μl) and dry dimethylformamide (4 ml) was heated at 80° C. for 2 hours. The solvent was then removed under reduced pressure and the residue was suspended in water. The precipitate was collected by filtration and recrystallized from a mixture of dichloromethane and methanol to give 50 mg of 10-[4-(3-carboxypropionyl)-1-piperazinyl]-9-fluoro-3-methyl-7-oxo-2,3-dihydro-7H-pyrido[3,2,1-ij]-1,3,4-benzoxadiazine-6-carboxylic acid, mp 257°-259° C. (dec.); FAB-MS m/z 449 (MH+).

EXAMPLE 50

Preparation of 10-(4-acetyl-1-piperazinyl)-9-fluoro-3-methyl-7-oxo-2,3-dihydro-7H-pyrido[3,2,1-ij]-1,3,4-benzoxadiazine-6-carboxylic acid 10-(4-Acetyl-1-piperazinyl)-9-fluoro-3-methyl-7-oxo-2,3-dihydro-7H-pyrido[3,2,1-ij]-1,3,4-benzoxadiazine-6-carboxylic acid was prepared from 9-fluoro-3-methyl-7-oxo-10-(1-piperazinyl)-2,3-dihydro-7H-pyrido[3,2,1-ij]-1,3,4-benzoxadiazine-6-carboxylic acid obtained in Example 6 and acetic anhydride, analogously to Example 49, and was obtained as crystals, mp 294°-296° C. (dec.); FAB-MS m/z 391 (MH+), after recrystallization from dichloromethane/methanol.

EXAMPLE 51

Preparation of 9-fluoro-3-methyl-7-oxo-10-[4-(3-oxo-n-butyl)-1-piperazinyl]-2,3-dihydro-7H-pyrido[3,2,1-ij]-1,3,4-benzoxadiazine-6-carboxylic acid A mixture of 9-fluoro-3-methyl-7-oxo-10-(1-piperazinyl)-2,3-dihydro-7H-pyrido[3,2,1-ij]-1,3,4-benzoxadiazine-6-carboxylic acid (30 mg) obtained in Example 6, methyl vinyl ketone (36 μl) and ethanol (1 ml) was refluxed for 12 hours, and then cooled to room temperature. The precipitate which separated out was collected by filtration and crystallized from ethanol to give 28 mg of 9-fluoro-3-methyl-7-oxo-10-[4-(3-oxo-n-butyl)-1-piperazinyl]-2,3-dihydro-7H-pyrido[3,2,1-ij]-1,3,4-benzoxadiazine-6-carboxylic acid, mp 187°-189° C. (dec.); FAB-MS m/z 419 (MH+).

EXAMPLE 52

Preparation of disodium 9-fluoro-3-methyl-7-oxo-10-[4-(sulfonatomethyl)-1-piperazinyl]-2,3-dihydro-7H-pyrido-[3,2,1-ij]-1,3,4-benzoxadiazine-6-carboxylate A mixture of 35% formalin (26 mg), sodium hydrogen sulfite (32 mg) and water (0.5 ml) was heated at 75° C. for 30 minutes and then cooled to room temperature. To this solution was added 9-fluoro-3-methyl-7-oxo-10-(1-piperazinyl)-2,3-dihydro-7H-pyrido[3,2,1-ij]-1,3,4-benzoxadiazine-6-carboxylic acid (100 mg) obtained in Example 6 and sodium hydroxide (15 mg). After the mixture was heated at 75° C. for 1 hour, ethanol (2 ml) was added. The mixture was then cooled to room temperature. The precipitate which separated out was collected by filtration and recrystallized from water/ethanol (1:2) to give disodium 9-fluoro-3-methyl-7-oxo-10-[4-(sulfonatomethyl)-1-piperazinyl]-2,3-dihydro-7H-pyrido[3,2,1-ij]-1,3,4-benzoxadiazine-6-carboxylate, mp 260°-263° C. (dec.); $^1$H NMR ($D_2O$) δ: 2.98 (3H, S), 3.05 (4H, m), 3.39 (4H, m), 3.84 (2H, S), 5.18 (2H, S), 7.55 (1H, d, J=13.4 Hz), 8.34 (1H, S).

EXAMPLE 53

Preparation of
10-[4-(4-aminobenzyl)-1-piperazinyl]-9-fluoro-3-methyl-7-oxo-2,3-dihydro-7H-pyrido[3,2,1-ij]-1,3,4-benzoxadiazine-6-carboxylic acid 9-Fluoro-3-methyl-10-[4-(4-nitrobenzyl)-1-piperazinyl]-7-oxo-2,3-dihydro-7H-pyrido[3,2,1-ij]-1,3,4-benzoxadiazine-6-carboxylic acid (100 mg) obtained in Example 47 was hydrogenated over 5% Pd/C (10 mg) in dichloromethane/methanol (1:1) for 2 hours. After removal of the catalyst by filtration, the filtrate was concentrated to dryness under reduced pressure. The residue was recrystallized from ethanol to give 69 mg of 10-[4-(4-aminobenzyl)-1-piperazinyl]-9-fluoro-3-methyl-7-oxo-2,3-dihydro-7H-pyrido[3,2,1-ij]-1,3,4-benzoxadiazine-6-carboxylic acid, mp 237°–238° C. (dec.); FAB-MS m/z 454 (MH+).

EXAMPLE 54

Preparation of
10-[3-(aminomethyl)-1-pyrrolidinyl]-9-fluoro-3-methyl-7-oxo-2,3-dihydro-7H-pyrido[3,2,1-ij]-1,3,4-benzoxadiazine-6-carboxylic acid The mixture of 10-[3-(acetylaminomethyl)-1-pyrrolidinyl]-9-fluoro-3-methyl-7-oxo-2,3-dihydro-7H-pyrido[3,2,1-ij]-1,3,4-benzoxadiazine-6-carboxylic acid (40 mg) obtained in Example 19 and 1N sodium hydroxide (2.5 ml) was heated at 100° C. for 3 hours. After cooling to room temperature, the reaction mixture was neutralized with acetic acid, and the precipitate which separated out was collected by filtration and recrystallized from methanol to give 15 mg of 10-[3-(aminomethyl)-1-pyrrolidinyl]-9-fluoro-3-methyl-7-oxo-2,3-dihydro-7H-pyrido[3,2,1-ij]-1,3,4-benzoxadiazine-6-carboxylic acid, mp 177°–180° C. (dec.); FAB-MS m/z 363 (MH+).

EXAMPLE 55

Preparation of
6-fluoro-8-hydroxy-7-(1-imidazolyl)-1-(methylamino)-4-oxo-1,4-dihydro-3-quinolinecarboxylic acid Carbonyldiimidazole (32 mg) was added to a stirred solution of 6,7-difluoro-8-hydroxy-1-(methylamino)-4-oxo-1,4-dihydro-3-quinolinecarboxylic acid (50 mg) obtained in Reference example (i) in dry dimethylformamide (2 ml). Stirring was continued at room temperature for 2 hours and then at 80° C. for 5 hours. The solvent was removed under reduced pressure and the residue was suspended in water and the pH was adjusted to pH 5 with acetic acid. The precipitate which separated out was filtered and washed with methanol to give 35 mg of 6-fluoro-8-hydroxy-7-(1-imidazolyl)-1-(methylamino)-4-oxo-1,4-dihydro-3-quinolinecarboxylic acid as pale yellow powder, FAB-MS m/z 319 (MH+); $^1$H-NMR (d$_6$-DMSO) δ: 2.82 (3H, s), 7.10 (1H, d, J=10.7 Hz), 7.61 (1H, d), 7.75 (1H, d), 8.62 (1H, s), 8.92 (1H, s), 15.33 (1H, br.s)

EXAMPLE 56

Preparation of
9-fluoro-10-(1-imidazolyl)-3-methyl-7-oxo-2,3-dihydro-7H-pyrido[3,2,1-ij]-1,3,4-benzoxadiazine-6-carboxylic acid A suspension of 6-fluoro-8-hydroxy-7-(1-imidazolyl)-1-(methylamino)-4-oxo-1,4-dihydro-3-quinolinecarboxylic acid (15 mg) obtained in Example 55 in a mixture of 35% formalin (1 ml) and dioxane (1 ml) was heated at 100°–110° C. for 1.5 hours under nitrogen atmosphere. The solvent was removed under reduced pressure and the crystalline residue was washed with methanol to give 15 mg of 9-fluoro-10-(1-imidazolyl)-3-methyl-7-oxo-2,3-dihydro-7H-pyrido[3,2,1-ij]-1,3,4-benzoxadiazine-6-carboxylic acid as pale pink powder. An analytical sample, mp>300° C.; FAB-MS m/z 331 (MH+) was prepared by recrystallization from dimethylformamide and ether.

9-Fluoro-10-(1-imidazolyl)-3-methyl-7-oxo-2,3-dihydro-7H-pyrido[3,2,1-ij]-1,3,4-benzoxadiazine-6-carboxylic acid was also prepared from 9,10-difluoro-3-methyl-7-oxo-2,3-dihydro-7H-pyrido[3,2,1-ij]-1,3,4-benzoxadiazine-6-carboxylic acid and imidazole in dimethylsulfoxide analogously to Example 5.

EXAMPLE 57

Preparation of benzyl
9-fluoro-10-(3-hydroxy-1-pyrrolidinyl)-3-methyl-7-oxo-2,3-dihydro-7H-pyrido[3,2,1-ij]-1,3,4-benzoxadiazine-6-carboxylate A mixture of 9-fluoro-10-(3-hydroxy-1-pyrrolidinyl)-3-methyl-7-oxo-2,3-dihydro-7H-pyrido[3,2,1-ij]-1,3,4-benzoxadiazine-6-carboxylic acid (10 mg) obtained in Example 21, anhydrous potassium carbonate (8 mg) and dimethylformamide (0.5 ml) was stirred at room temperature for 1.5 hours and then benzylbromide (10.8 mg) was added. This mixture was stirred at room temperature for 3 hours and evaporated under reduced pressure.

The residue was suspended in water and extracted with chloroform. The extract was concentrated to dryness under reduced pressure. The residue was triturated with ether to give 11 mg of benzyl 9-fluoro-10-(3-hydroxy-1-pyrrolidinyl)-3-methyl-7-oxo-2,3-dihydro-7H-pyrido[3,2,1-ij]-1,3,4-benzoxadiazine-6-carboxylate, mp 196°–198° C. (dec.); FAB-MS m/z 440 (MH+).

EXAMPLE 58

Preparation of benzyl
10-(3-chloro-1-pyrrolidinyl)-9-fluoro-3-methyl-7-oxo-2,3-dihydro-7H-pyrido[3,2,1-ij]-1,3,4-benzoxadiazine-6-carboxylate Benzyl 9-fluoro-10-(3-hydroxy-1-pyrrolidinyl)-3-methyl-7-oxo-2,3-dihydro-7H-pyrido[3,2,1-ij]-1,3,4-benzoxadiazine-6-carboxylate (8 mg) obtained in Example 57 was dissolved in 0.2 ml of thionyl chloride and stirred at 60° C. for 15 minutes. The reaction mixture was diluted with water and extracted with chloroform. The extract was concentrated under reduced pressure. The residue was chromatographed on silica gel (2 g) with chloroform to give 2.8 mg of benzyl 10-(3-chloro-1-pyrrolidinyl)-9-fluoro-3-methyl-7-oxo-2,3-dihydro-7H-pyrido-[3,2,1-ij]-1,3,4-benzoxadiazine-6-carboxylate, mp>300° C.; FAB-MS m/z 458 (MH+), 460 (MH+2)+.

EXAMPLE 59

Preparation of
10-(3-chloro-1-pyrrolidinyl)-9-fluoro-3-methyl-7-oxo-2,3-dihydro-7H-pyrido[3,2,1-ij]-1,3,4-benzoxadiazine-6-carboxylic acid Benzyl 10-(3-chloro-1-pyrrolidinyl)-9-fluoro-3-methyl-7-oxo-2,3-dihydro-7H-pyrido[3,2,1-ij]-1,3,4-benzoxadiazine-6-carboxylate (2.5 mg) obtained in Example 58 was hydrogenated over 5% Pd/C (1 mg) in chloroform.

After removal of the catalyst by filtration, the filtrate was concentrated to dryness under reduced pressure. The residue was recrystallized from ethanol to give 1.0 mg of 10-(3-chloro-1-pyrrolidinyl)-9-fluoro-3-methyl-7-oxo-2,3-dihydro-7H-pyrido[3,2,1-ij]-1,3,4-benzoxadiazine-6-carboxylic acid, mp 269°–272° C. (dec.); FAB-MS m/z 368 (MH+), 370 (MH+2)+.

EXAMPLE 60

Preparation of 9-fluoro-3-methyl-10-(4-methyl-1-piperazinyl)-7-oxo-2,3-dihydro-7H-pyrido[3,2,1-ij]-1,3,4-benzoxadiazine-6-carboxylic acid via the fluoroborane intermediate (a) A mixture of 9,10-difluoro-3-methyl-7-oxo-2,3-dihydro-7H-pyrido[3,2,1-ij]-1,3,4-benzoxadiazine-6-carboxylic acid (100 mg) obtained in Example 1 and 60% aqueous fluoboric acid (1 ml) was heated at 90° C. for 12 hours. After the reaction mixture was cooled to room temperature the precipitate was collected by filtration, washed with methanol and dried under reduced pressure to give 110 mg of crude 9,10-difluoro-6-[[(difluoroboryl)oxy]carbonyl]-3-methyl-2,3-dihydro-7H-pyrido[3,2,1-ij]-1,3,4-benzoxadiazin-7-one; FAB-MS m/z 331 (MH+).

(b) To a stirred solution of the above borane intermediate (33 mg) in dimethylsulfoxide (1 ml) were added N-methylpiperazine (15 µl) and triethylamine (20 µl). After stirring at room temperature for 3 hours the reaction mixture was lyophilized. The residue was crystallized from methanol to give 28 mg of 6-[[(difluoroboryl)oxy]carbonyl]-9-fluoro-3-methyl-10-(4-methyl-1-piperazinyl)-2,3-dihydro-7H-pyrido[3,2,1-ij]-1,3,4-benzoxadiazin-7-one as yellow crystals, mp 228°–230° C. (dec.); FAB-MS m/z 411 (MH+).

(c) To a solution of the above borane intermediate (5 mg) in 95% ethanol (1 ml) was added triethylamine (3 µl). After heating under reflux for 4 hours, the reaction mixture was cooled to room temperature. The precipitate which separated out was collected by filtration to give 9-fluoro-3-methyl-10-(4-methyl-1-piperazinyl)-7-oxo-2,3-dihydro-7H-pyrido-[3,2,1-ij]-1,3,4-benzoxadiazine-6-carboxylic acid, mp 268°–269° C. (dec.).

EXAMPLE 61

Preparation of 9-fluoro-3-methyl-10-(4-methyl-1-piperazinyl)-7-oxo-2,3-dihydro-7H-pyrido[3,2,1-ij]-1,3,4-benzoxadiazine-6-carboxylic acid via the acetoxyborane intermediate (a) A mixture of 9,10-difluoro-3-methyl-7-oxo-2,3-dihydro-7H-pyrido[3,2,1-ij]-1,3,4-benzoxadiazine-6-carboxylic acid (100 mg) obtained in Example 1, acetic anhydride (1 ml) and triacetoxyborane (100 mg) was heated at 140° C. for 15 minutes. The reaction mixture was evaporated under reduced pressure. The residue was triturated with acetone and filtered to give 138 mg of 6-[[(diacetoxyboryl)oxy]carbonyl]-9,10-difluoro-3-methyl-2,3-dihydro-7H-pyrido[3,2,1-ij]-1,3,4-benzoxadiazin-7-one; FAB-MS m/z 411 (MH+).

(b) To a solution of the above borane intermediate (41 mg) in dimethylsulfoxide (1 ml) were added N-methylpiperazine (15 µl) and triethylamine (20 µl). After the mixture was stirred at room temperature for 2 hours, the reaction mixture was lyophilized. The residue was crystallized from methanol/ether to give 34 mg of 6-[[(diacetoxyboryl)oxy]carbonyl]-9-fluoro-3-methyl-10-(4-methyl-1-piperazinyl)-2,3-dihydro-7H-pyrido[3,2,1-ij]-1,3,4-benzoxadiazin-7-one as yellow crystals; mp 156°–157° C. (dec.); FAB-MS m/z 491 (MH+).

(c) The above borane intermediate (5 mg) was suspended in acetone (0.1 ml) and added conc. HCl (2.5 µl). The reaction mixture was stirred at room temperature for 30 minutes and cooled in ice bath. The precipitate which separated out was collected by filtration and the precipitate was dissolved in 95% ethanol (0.1 ml). To the solution was added triethylamine (2 µl) and the mixture was refluxed for 1 hour. After the solution was cooled to room temperature, the precipitate which separated out was collected by filtration to give 9-fluoro-3-methyl-10-(4-methyl-1-piperazinyl)-7-oxo-2,3-dihydro-7H-pyrido[3,2,1-ij]-1,3,4-benzoxadiazine-6-carboxylic acid, mp 268°–269° C. (dec.).

EXAMPLE 62

Preparation of pivaloyloxymethyl 10-[3-(benzyloxycarbonylamino)-1-pyrrolidinyl]-9-fluoro-3-methyl-7-oxo-2,3-dihydro-7H-pyrido[3,2,1-ij]-1,3,4-benzoxadiazine-6-carboxylate A mixture of 10-[3-(benzyloxycarbonylamino)-1-pyrrolidinyl]-9-fluoro-3-methyl-7-oxo-2,3-dihydro-7H-pyrido-[3,2,1-ij]-1,3,4-benzoxadiazine-6-carboxylic acid (290 mg) obtained in Example 29, pivaloyloxymethyl chloride (130 µl), anhydrous potassium carbonate (166 mg) and dry dimethylformamide (10 ml) was stirred at 45° C. for 8 hours. The solvent was then removed under reduced pressure. The residue was dissolved in dichloromethane. The dichloromethane solution was washed with water and dried over anhydrous sodium sulfate. The solvent was evaporated off under reduced pressure and the residue was recrystallized from ethyl acetate to give 325 mg of pivaloyloxymethyl 10-[3-(benzyloxycarbonylamino)-1-pyrrolidinyl]-9-fluoro-3-methyl-7-oxo-2,3-dihydro-7H-pyrido[3,2,1-ij]-1,3,4-benzoxadiazine-6-carboxylate; mp 185°–188° C.; FAB-MS m/z 597 (MH+).

EXAMPLE 63

Preparation of pivaloyloxymethyl 10-(3-amino-1-pyrrolidinyl)-9-fluoro-3-methyl-7-oxo-2,3-dihydro-7H-pyrido[3,2,1-ij]-1,3,4-benzoxadiazine-6-carboxylate Pivaloyloxymethyl 10-(3-amino-1-pyrrolidinyl)-9-fluoro-3-methyl-7-oxo-2,3-dihydro-7H-pyrido[3,2,1-ij]-1,3,4-benzoxadiazine-6-carboxylate was prepared from pivaloyloxymethyl 10-[3-(benzyloxycarbonylamino)-1-pyrrolidinyl]-9-fluoro-3-methyl-7-oxo-2,3-dihydro-7H-pyrido[3,2,1-ij]-1,3,4-benzoxadiazine-6-carboxylate (200 mg) obtained in Example 62, analogously to Example 30, and was obtained as pale brown powder after precipitation from a mixture of ethyl acetate and n-hexane; $^1$H NMR (CDCl$_3$) δ: 1.22 (9H, s), 1.6–2.4 (2H, m), 2.99 (3H, s), 3.3–4.0 (5H, m), 4.98 (2H, s), 5.96 (2H, s), 7.64 (1H, d, J=14.4 Hz), 8.37 (1H, s); FAB-MS m/z 463 (MH+).

EXAMPLE 64

Preparation of ethyl 10-[3-(benzyloxycarbonylamino)-1-pyrrolidinyl]-9-fluoro-3-methyl-7-oxo-2,3-dihydro-7H-pyrido-[3,2,1-ij]-1,3,4-benzoxadiazine-6-carboxylate A mixture of 10-[3-(benzyloxycarbonylamino)-1-pyrrolidinyl]-9-fluoro-3-methyl-7-oxo-2,3-dihydro-7H-pyrido[3,2,1-ij]-1,3,4-benzoxadiazine-6-carboxylic acid (337 mg) obtained in Example 29, ethyl iodide (84 μl), anhydrous potassium carbonate (193 mg) and dry dimethylformamide (12 ml) was stirred at 45° C. for 6 hours. The solvent was removed under reduced pressure, and the residue was dissolved in dichloromethane. The dichloromethane solution was washed with water, dried over anhydrous sodium sulfate and concentrated under reduced pressure. The residue was then applied onto a column of silica gel and eluted with a mixture of chloroform and acetone (20:1). The pure fractions were combined, concentrated to dryness under reduced pressure and the residue was recrystallized from ethyl acetate to give 271 mg of ethyl 10-[3-(benzyloxycarbonylamino)-1-pyrrolidinyl]-9-fluoro-3-methyl-7-oxo-2,3-dihydro-7H-pyrido-[3,2,1-ij]-1,3,4-benzoxadiazine-6-carboxylate, mp 204°–207° C.; FAB-MS m/z 511 (MH+).

EXAMPLE 65

Preparation of ethyl 10-(3-amino-1-pyrrolidinyl)-9-fluoro-3-methyl-7-oxo-2,3-dihydro-7H-pyrido[3,2,1-ij]-1,3,4-benzoxadiazine-6-carboxylate Ethyl 10-[3-(benzyloxycarbonylamino)-1-pyrrolidinyl]-9-fluoro-3-methyl-7-oxo-2,3-dihydro-7H-pyrido[3,2,1-ij]-1,3,4-benzoxadiazine-6-carboxylate (200 mg) obtained in Example 64 was hydrogenated over 5% Pd/C (120 mg) in a mixture of chloroform (25 ml) and methanol (10 ml) for 23 hours. After removal of the catalyst by filtration the filtrate was concentrated under reduced pressure. The residue was then applied onto a column of silica gel, and eluted with a mixture of chloroform and methanol (4:1). The pure fractions were combined and concentrated to dryness under reduced pressure. The residue was further purified by preparative TLC (silica gel; CHCl₃/MeOH, 3:1) and recrystallized from ethanol to give 71 mg of ethyl 10-(3-amino-1-pyrrolidinyl)-9-fluoro-3-methyl-7-oxo-2,3-dihydro-7H-pyrido[3,2,1-ij]-1,3,4-benzoxadiazine-6-carboxylate, mp 187°–192° C. (dec.); FAB-MS m/z 377 (MH+).

EXAMPLE 66

Preparation of 10-(3-amino-1-pyrrolidinyl)-9-fluoro-3-methyl-7-oxo-2,3-dihydro-7H-pyrido[3,2,1-ij]-1,3,4-benzoxadiazine-6-carboxylic acid hydrochloride The pH of a solution of 10-(3-amino-1-pyrrolidinyl)-9-fluoro-3-methyl-7-oxo-2,3-dihydro-7H-pyrido[3,2,1-ij]-1,3,4-benzoxadiazine-6-carboxylic acid (20 mg) obtained in Example 30 in water (1 ml) was adjusted to 1.0 with 6N-HCl. The clear solution was then lyophilized and the residue was crystallized from water/ethanol (1:2) to give 19 mg of 10-(3-amino-1-pyrrolidinyl)-9-fluoro-3-methyl-7-oxo-2,3-dihydro-7H-pyrido[3,2,1-ij]-1,3,4-benzoxadiazine-6-carboxylic acid hydrochloride, mp 226°–228° C. (dec.).

EXAMPLE 67

Preparation of 9-fluoro-3-methyl-10-(4-methyl-1-piperazinyl)-7-oxo-2,3-dihydro-7H-pyrido[3,2,1-ij]-1,3,4-benzoxadiazine-6-carboxylic acid hydrochloride 9-Fluoro-3-methyl-10-(4-methyl-1-piperazinyl)-7-oxo-2,3-dihydro-7H-pyrido[3,2,1-ij]-1,3,4-benzoxadiazine-6-carboxylic acid hydrochloride was obtained analogously to Example 66, mp 264°–266° C. (dec.).

EXAMPLE 68

Preparation of sodium 9-fluoro-3-methyl-10-morpholino-7-oxo-2,3-dihydro-7H-pyrido[3,2,1-ij]-1,3,4-benzoxadiazine-6-carboxylate 9-Fluoro-3-methyl-10-morpholino-7-oxo-2,3-dihydro-7H-pyrido[3,2,1-ij]-1,3,4-benzoxadiazine-6-carboxylic acid (14 mg) obtained in Example 9 was suspended in water (0.4 ml), and 1N sodium hydroxide (40 μl) was added with stirring. The clear solution was lyophilized and the residue was crystallized from water/ethanol (1:4) to give 12 mg of sodium 9-fluoro-3-methyl-10-morpholino-7-oxo-2,3-dihydro-7H-pyrido[3,2,1-ij]-1,3,4-benzoxadiazine-6-carboxylate, mp >300° C.

EXAMPLE 69

Preparation of 9-fluoro-3-(2-fluoroethyl)-10-(4-methyl-1-piperazinyl)-7-oxo-2,3-dihydro-7H-pyrido[3,2,1-ij]-1,3,4-benzoxadiazine-6-carboxylic acid 9-Fluoro-3-(2-fluoroethyl)-10-(4-methyl-1-piperazinyl)-7-oxo-2,3-dihydro-7H-pyrido[3,2,1-ij]-1,3,4-benzoxadiazine-6-carboxylic acid was prepared from ethyl 8-benzyloxy-6,7-difluoro-1-(formylamino)-4-oxo-1,4-dihydro-3-quinolinecarboxylate obtained in Reference example (f), following a series of procedures of Reference example (g, h and i) (using 1-bromo-2-fluoroethane instead of methyl iodide), Example 1 and Example 5, and was obtained as crystals, mp 220°–224° C.; MS m/z 394 (M+) after recrysallization from methanol.

EXAMPLES 70–77

There were obtained the following compounds starting from the compound obtained in Example 1 by using a manner analogous to the one described in Example 5 or Examples 29/30.

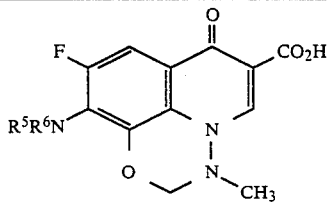

| Example No. | R⁵R⁶N— | Melting point °C. | Recrystallization solvent | FAB-MS m/Z |
|---|---|---|---|---|
| 70 | CH₃N⟨piperazine⟩N—⟨pyrrolidine⟩N— | 262 (dec.) | MeOH | 432 (MH⁺) |
| 71 | CH₃O | 221–230 (dec.) | EtOH/hexane | 379 (MH⁺) |
| 72 | CH H₂N—⟨pyrrolidine⟩N— | 240–245 (dec.) | EtOH/hexane | 365 (MH⁺) |
| 73 | Ph H₂N—⟨pyrrolidine⟩N— | 253–255 (dec.) | MeOH/ether | 425 (MH⁺) |
| 74 | CH₃ H₂N—⟨pyrrolidine⟩N— | 240–241 | MeOH | 363 (MH⁺) |
| 75 | CH₃—⟨pyrrolidine⟩N— H₂N | >300 (dec.) | EtOH/CHCl₃/hexane | 363 (MH⁺) |
| 76 | Ph H CH₃N—⟨pyrrolidine⟩N— | 220–223 (dec.) | EtOH | 453 (MH⁺) |
| 77 | CH₃ H CH₃N—⟨pyrrolidine⟩N— | 211–214 (dec.) | EtOH/CHCl₃ | 391 (MH⁺) |

The following compounds starting from the compound obtained in Example 1 could be also obtained according to a manner analogous to that of Example 5 or Examples 29/30.

10-[3-(aminomethyl)-4-methyl-1-pyrrolidinyl]-9-fluoro-3-methyl-7-oxo-2,3-dihydro-7H-pyrido[3,2,1-ij]-1,3,4-benzoxadiazine-6-carboxylic acid, 10-[3-[(ethylamino)methyl]-4-methyl-1-pyrrolidinyl]-9-fluoro-3-methyl-7-oxo-2,3-dihydro-7H-pyrido[3,2,1-ij]-1,3,4-benzoxadiazine-6-carboxylic acid, 10-[3-(aminomethyl)-4-chloro-1-pyrrolidinyl]-9-fluoro-3-methyl-7-oxo-2,3-dihydro-7H-pyrido[3,2,1-ij]-1,3,4-benzoxadiazine-6-carboxylic acid, 10-[3-(aminomethyl)-4-fluoro-1-pyrrolidinyl]-9-fluoro-3-methyl-7-oxo-2,3-dihydro-7H-pyrido[3,2,1-ij]-1,3,4-benzoxadiazine-6-carboxylic acid, 10-[3-chloro-4-[(methylamino)methyl]-1-pyrrolidinyl]-9-fluoro-3-methyl-7-oxo-2,3-dihydro-7H-pyrido[3,2,1-ij]-1,3,4-benzoxadiazine-6-carboxylic acid, 9-fluoro-10-[3-fluoro-4-[(methylamino)methyl]-1-pyrrolidinyl]-3-methyl-7-oxo-2,3-dihydro-7H-pyrido[3,2,1-ij]-1,3,4-benzoxadiazine-6-carboxylic acid, 10-[3-chloro-4-[(ethylamino)methyl]-1-pyrrolidinyl]-9-fluoro-3-methyl-7-oxo-2,3-dihydro-7H-pyrido[3,2,1-ij]-1,3,4-benzoxadiazine-6-carboxylic acid, 10-[3-[(ethylamino)methyl]-4-fluoro-1-pyrrolidinyl]-9-fluoro-3-methyl-7-oxo-2,3-dihydro-7H-pyrido[3,2,1-ij]-1,3,4-benzoxadiazine-6-carboxylic acid, 9-fluoro-10-[3-methoxy-4-(methylamino)-1-pyrrolidinyl]-3-methyl-7-oxo-2,3dihydro-7H-pyrido[3,2,1-ij]-1,3,4-benzoxadiazine-6-carboxylic acid, 10-[3-(ethylamino)-4-methoxy-1-pyrrolidinyl]-9-fluoro-3-methyl-7-oxo-2,3-dihydro-7H-pyrido[3,2,1-ij]-1,3,4-benzoxadiazine-6-carboxylic acid, 9-fluoro-10-(3-hydroxy-4-methoxy-1-pyrrolidinyl)-3-methyl-7-oxo-2,3-dihydro-7H-pyrido[3,2,1-ij]-1,3,4-benzoxadiazine-6-carboxylic acid, 10-(3-amino-4-chloro-1-pyrrolidinyl)-9-fluoro-3-methyl-7-oxo-2,3-dihydro-7H-pyrido[3,2,1-ij]-1,3,4-benzoxadiazine-6-carboxylic acid, 10-(3-amino-4-fluoro-1-pyrrolidinyl)-9-fluoro-3-methyl-7-oxo-2,3-dihydro-7H-pyrido[3,2,1-ij]-1,3,4-benzoxadiazine-6-carboxylic acid, 10-[3-chloro-4-(methylamino)-1-pyrrolidinyl]-9-fluoro-3-methyl-7-oxo-2,3-dihydro-7H-pyrido[3,2,1-ij]-1,3,4-benzoxadiazine-6-carboxylic acid, 9-fluoro-10-[3-fluoro-4-(methylamino)-1-pyrrolidinyl]-3-methyl-7-oxo-2,3-dihydro-7H-pyrido[3,2,1-ij]-1,3,4-benzoxadiazine-6-carboxylic acid, 9-fluoro-3-methyl-10-(1-oxide-4-thiomorpholinyl)-7-oxo-2,3-dihydro-7H-pyrido[3,2,1-ij]-1,3,4-benzoxadiazine-6-carboxylic acid, 9-fluoro-10-[3-hydroxy-4-(methylamino)-1-pyrrolidinyl]-3-methyl-7-oxo-2,3-dihydro-7H-pyrido[3,2,1-ij]-1,3,4-benzoxadiazine-6-carboxylic acid.

EXAMPLE 78

Preparation of 10-[3-[(4-aminobenzyl)amino]-1-pyrrolidinyl]-9-fluoro-3-methyl-7-oxo-2,3-dihydro-7H-pyrido[3,2,1-ij]-1,3,4-benzoxadiazine-6-carboxylic acid 10-[3-[(4-Aminobenzyl)amino]-1-pyrrolidinyl]-9-fluoro-3-methyl-7-oxo-2,3-dihydro-7H-pyrido[3,2,1-ij]-1,3,4-benzoxadiazine-6-carboxylic acid was prepared analogously to the methods described in Example 47 and 53, starting from 10-(3-amino-1-pyrrolidinyl)-9-fluoro-3-methyl-7-oxo-2,3-dihydro-7H-pyrido[3,2,1-ij]-1,3,4-benzoxadiazine-6-carboxylic acid which was obtained in Example 30; mp. 180°–182° C. (dec.), FAB-MS m/z 453 (MH+).

EXAMPLE 79

Preparation of 9-fluoro-10-[3-[[(dimethylamino)methylene]-amino]-1-pyrrolidinyl]-3-methyl-7-oxo-2,3-dihydro-7H-pyrido-[3,2,1-ij]-1,3,4-benzoxadiazine-6-carboxylic acid A suspension of 10-(3-amino-1-pyrrolidinyl)-9-fluoro-3-methyl-7-oxo-2,3-dihydro-7H-pyrido[3,2,1-ij]-1,3,4-benzoxadiazine-6-carboxylic acid (14 mg) obtained in Example 30 and N,N-dimethylformamide dimethylacetal (6 μl) in dry DMF (0.5 ml) was stirred at room temperature for 8.5 hours. The precipitate was collected by filtration, washed with DMF and ether, and recrystallized from DMF to give 8 mg of 9-fluoro-10-[3-[[(dimethylamino)methylene]amino]-1-pyrrolidinyl]-3-methyl-7-oxo-2,3-dihydro-7H-pyrido[3,2,1-ij]-1,3,4-benzoxadiazine-6-carboxylic acid as pale yellow crystals; mp. 218°–220° C. (dec.), FAB-MS m/z 404 (MH+).

EXAMPLE 80

Preparation of sodium 9-fluoro-3-methyl-10-(4-methyl-1-piperazinyl)-7-oxo-2,3-dihydro-7H-pyrido[3,2,1-ij]-1,3,4-benzoxadiazine-6-carboxylate 9-Fluoro-3-methyl-10-(4-methyl-1-piperazinyl)-7-oxo-2,3-dihydro-7H-pyrido[3,2,1-ij]-1,3,4-benzoxadiazine-6-carboxylic acid (520 mg) was dissolved in 0.5N sodium hydroxide (2.88 ml). The clear solution was evaporated under reduced pressure to give 555 mg of pale yellow powder, which was recrystallized from ethanol to give 475 mg of sodium 9-fluoro-3-methyl-10-(4-methyl-1-piperazinyl)-7-oxo-2,3-dihydro-7H-pyrido[3,2,1-ij]-1,3,4-benzoxadiazine-6-carboxylate, after drying in vacuo at 80° C. for 2 days; mp 252°–254° C. (dec.), FAB-MS m/z 385.

The following Examples illustrate pharmaceutical preparations containing a compound provided by the present invention:

EXAMPLE A

Interlocking gelatin capsules each containing the following ingredients were manufactured in the conventional manner per se:

| | |
|---|---|
| 9-Fluoro-3-methyl-10-(4-methyl-1-piperazinyl)-7-oxo-2,3-dihydro-7H—pyrido[3,2,1-ij]-1,3,4-benzoxadiazine-6-carboxylic acid | 200 mg |
| Luviskol (water-soluble polyvinylpyrrolidone) | 20 mg |
| Mannitol | 20 mg |
| Talc | 15 mg |
| Magnesium stearate | 2 mg |
| | 257 mg |

EXAMPLE B

Tablets each containing the following ingredients were manufactured in the conventional manner per se:

| | |
|---|---|
| 9-Fluoro-3-methyl-10-(4-methyl-1-piperazinyl)-7-oxo-2,3-dihydro-7H—pyrido[3,2,1-ij]-1,3,4-benzoxadiazine-6-carboxylic acid | 200 mg |
| Starch | 44 mg |

| -continued | |
|---|---|
| Carboxymethylcellulose calcium | 30 mg |
| Crystalline cellulose | 40 mg |
| Magnesium stearate | 6 mg |
| | 320 mg |

What we claim is:

1. A compound of the formula:

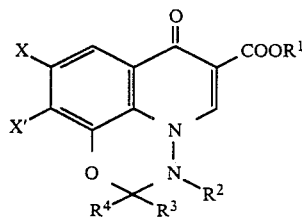
(III)

wherein $R^1$ is a hydrogen atom or a carboxy-protecting radical; $R^2$ is a hydrogen atom or a lower alkyl radical which may be substituted with a halogen atom; $R^3$ and $R^4$ independently are a hydrogen atom or a lower alkyl radical which may be substituted with a hydroxy radical or a substituted or unsubstituted amino radical; and X and X', which are the same or different, are halogen atoms.

* * * * *